US011464767B2

(12) United States Patent
Donovan et al.

(10) Patent No.: US 11,464,767 B2
(45) Date of Patent: *Oct. 11, 2022

(54) PRODRUGS OF PHENOLIC TRPV1 AGONISTS IN COMBINATION WITH LOCAL ANESTHETICS AND VASOCONSTRICTORS FOR IMPROVED LOCAL ANESTHESIA

(71) Applicant: Concentric Analgesics, Inc., San Francisco, CA (US)

(72) Inventors: John F. Donovan, San Francisco, CA (US); Craig Husfeld, San Mateo, CA (US)

(73) Assignee: CONCENTRIC ANALGESICS, INC., San Francisco, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 17/031,729

(22) Filed: Sep. 24, 2020

(65) Prior Publication Data

US 2021/0008050 A1 Jan. 14, 2021

Related U.S. Application Data

(63) Continuation of application No. 16/303,082, filed as application No. PCT/US2017/034318 on May 24, 2017, now Pat. No. 10,821,105.

(60) Provisional application No. 62/341,529, filed on May 25, 2016.

(51) Int. Cl.
*A61K 31/445* (2006.01)
*A61K 45/06* (2006.01)
*A61K 31/165* (2006.01)
*A61K 31/137* (2006.01)
*A61P 29/00* (2006.01)

(52) U.S. Cl.
CPC .......... *A61K 31/445* (2013.01); *A61K 31/137* (2013.01); *A61K 31/165* (2013.01); *A61K 45/06* (2013.01); *A61P 29/00* (2018.01)

(58) Field of Classification Search
None
See application file for complete search history.

(56) References Cited

U.S. PATENT DOCUMENTS

| 3,598,122 A | 8/1971 | Zaffaroni |
|---|---|---|
| 3,598,123 A | 8/1971 | Zaffaroni |
| 3,710,795 A | 1/1973 | Higuchi et al. |
| 3,731,683 A | 5/1973 | Zaffaroni et al. |
| 3,742,951 A | 7/1973 | Zaffaroni et al. |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,151,273 A | 4/1979 | Riegelman et al. |
| 4,201,211 A | 5/1980 | Chandrasekaran et al. |
| 4,229,447 A | 10/1980 | Porter |
| 4,230,105 A | 10/1980 | Harwood |
| 4,292,299 A | 9/1981 | Suzuki et al. |
| 4,292,303 A | 9/1981 | Keith et al. |
| 4,327,725 A | 5/1982 | Cortese et al. |
| 4,343,789 A | 8/1982 | Kawata et al. |
| 4,476,116 A | 10/1984 | Anik |
| 4,596,795 A | 6/1986 | Pitha |
| 4,624,848 A | 11/1986 | Lee |
| 4,755,386 A | 7/1988 | Hsiao et al. |
| 4,812,590 A | 3/1989 | Saari |
| 4,871,549 A | 10/1989 | Ueda et al. |
| 4,935,368 A | 6/1990 | Kotani et al. |
| 4,968,509 A | 11/1990 | Radebaugh et al. |
| 5,011,692 A | 4/1991 | Fujioka et al. |
| 5,017,381 A | 5/1991 | Maruyama et al. |
| 5,094,782 A | 3/1992 | Chen et al. |
| 5,116,817 A | 5/1992 | Anik |
| 5,229,135 A | 7/1993 | Philippon et al. |
| 5,260,068 A | 11/1993 | Chen |
| 5,260,069 A | 11/1993 | Chen |
| 5,281,420 A | 1/1994 | Kelm et al. |
| 5,336,168 A | 8/1994 | Sibalis |
| 5,340,591 A | 8/1994 | Nakano et al. |

(Continued)

FOREIGN PATENT DOCUMENTS

| CN | 1750839 A | 3/2006 |
|---|---|---|
| CN | 101208294 A | 6/2008 |

(Continued)

OTHER PUBLICATIONS

Iftinca et al., "TRPV1-Targeted Drugs in Development for Human Pain Conditions", 2021, Drugs, 81(1), pp. 7-27. (doi.org/10.1007/s40265-020-01429-2) (Year: 2021).*

(Continued)

*Primary Examiner* — My-Chau T. Tran

(74) *Attorney, Agent, or Firm* — Wilson Sonsini Goodrich & Rosati

(57) ABSTRACT

Described herein are compounds, pharmaceutical compositions and medicaments that include such compounds, and methods of using such compounds to modulate transient receptor potential vanilloid 1 receptor (TRPV1) activity.

8 Claims, 5 Drawing Sheets

(56) References Cited

U.S. PATENT DOCUMENTS

| | | |
|---|---|---|
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,567,441 A | 10/1996 | Chen |
| 5,622,721 A | 4/1997 | Dansereau et al. |
| 5,665,378 A | 9/1997 | Davis et al. |
| 5,686,105 A | 11/1997 | Kelm et al. |
| 5,700,410 A | 12/1997 | Nakamichi et al. |
| 5,700,485 A | 12/1997 | Berde et al. |
| 5,723,269 A | 3/1998 | Akagi et al. |
| 5,739,136 A | 4/1998 | Ellinwood, Jr. et al. |
| 5,837,280 A | 11/1998 | Kenealy et al. |
| 5,837,284 A | 11/1998 | Mehta et al. |
| 5,840,329 A | 11/1998 | Bai |
| 5,858,401 A | 1/1999 | Bhalani et al. |
| 5,869,090 A | 2/1999 | Rosenbaum |
| 5,962,532 A | 10/1999 | Campbell et al. |
| 5,977,175 A | 11/1999 | Lin |
| 6,083,518 A | 7/2000 | Lindahl |
| 6,391,452 B1 | 5/2002 | Antonsen et al. |
| 6,465,014 B1 | 10/2002 | Moroni et al. |
| 6,667,048 B1 | 12/2003 | Lambert et al. |
| 6,923,983 B2 | 8/2005 | Morgan et al. |
| 6,929,801 B2 | 8/2005 | Klose et al. |
| 6,932,983 B1 | 8/2005 | Straub et al. |
| 6,946,144 B1 | 9/2005 | Jordan |
| 6,960,563 B2 | 11/2005 | Egbaria et al. |
| 7,632,519 B2 | 12/2009 | Jamieson et al. |
| 7,632,539 B2 | 12/2009 | Miyake |
| 7,943,666 B2 | 5/2011 | Singh et al. |
| 8,217,005 B2 | 7/2012 | Jenkins et al. |
| 8,367,733 B2 | 2/2013 | Burch et al. |
| 8,420,600 B2 | 4/2013 | Burch et al. |
| 8,497,237 B2 | 7/2013 | Jenkins et al. |
| 8,569,228 B2 | 10/2013 | Jenkins et al. |
| 8,685,916 B2 | 4/2014 | Jenkins et al. |
| 8,802,681 B2 | 8/2014 | Jenkins et al. |
| 9,040,032 B2 | 5/2015 | Jenkins et al. |
| 9,139,612 B2 | 9/2015 | Jenkins et al. |
| 9,238,020 B2 | 1/2016 | Jenkins et al. |
| 9,359,316 B1 | 6/2016 | Husfeld et al. |
| 10,717,712 B2 * | 7/2020 | Donovan ............ C07D 241/04 |
| 10,821,105 B2 * | 11/2020 | Donovan ............ A61K 31/445 |
| 11,242,325 B2 * | 2/2022 | Donovan ............ C07D 241/04 |
| 2004/0013734 A1 | 1/2004 | Babcock et al. |
| 2004/0156931 A1 | 8/2004 | Burch et al. |
| 2006/0240097 A1 | 10/2006 | Jamieson et al. |
| 2008/0020996 A1 | 1/2008 | Singh et al. |
| 2008/0193481 A1 | 8/2008 | Bundle et al. |
| 2010/0152434 A1 | 6/2010 | Peterson |
| 2010/0227921 A1 | 9/2010 | Franklin et al. |
| 2011/0243884 A1 | 10/2011 | O'Shea et al. |
| 2011/0262359 A1 | 10/2011 | Jenkins et al. |
| 2011/0262360 A1 | 10/2011 | Jenkins et al. |
| 2012/0232066 A1 | 9/2012 | Jenkins et al. |
| 2012/0270847 A1 | 10/2012 | Franklin et al. |
| 2013/0035635 A1 | 2/2013 | Rau et al. |
| 2013/0079364 A1 | 3/2013 | Jenkins et al. |
| 2013/0089504 A1 | 4/2013 | Jenkins et al. |
| 2015/0119423 A1 | 4/2015 | Kandula et al. |
| 2016/0136153 A1 | 5/2016 | Jenkins |
| 2017/0100390 A1 | 4/2017 | Jenkins |
| 2017/0159100 A1 | 6/2017 | Hasserodt et al. |
| 2017/0260131 A1 | 9/2017 | Husfeld et al. |
| 2019/0055272 A1 | 2/2019 | Husfeld et al. |
| 2019/0216787 A1 | 7/2019 | Donovan et al. |
| 2019/0284132 A1 | 9/2019 | Husfeld et al. |
| 2020/0299245 A1 | 9/2020 | Donovan et al. |
| 2022/0112165 A1 | 4/2022 | Donovan et al. |

FOREIGN PATENT DOCUMENTS

| | | |
|---|---|---|
| CN | 101774938 A | 7/2010 |
| CN | 102205127 A | 10/2011 |
| CN | 104447777 A | 3/2015 |
| EP | 1201649 A1 | 5/2002 |
| EP | 2774915 A1 | 9/2014 |
| JP | H04368359 A | 12/1992 |
| JP | 2004511488 A | 4/2004 |
| JP | 2007525431 A | 9/2007 |
| JP | 2012505161 A | 3/2012 |
| KR | 101478520 B1 | 1/2015 |
| WO | WO-2006116485 A2 | 11/2006 |
| WO | WO-2011133149 A1 | 10/2011 |
| WO | WO-2011133150 A1 | 10/2011 |
| WO | WO-2012098557 A1 | 7/2012 |
| WO | WO-2013175376 A2 | 11/2013 |
| WO | WO-2016086063 A1 | 6/2016 |
| WO | WO-2017147146 A1 | 8/2017 |
| WO | WO-2017205534 A1 | 11/2017 |
| WO | WO-2020023793 A1 | 1/2020 |
| WO | WO-2020023794 A1 | 1/2020 |

OTHER PUBLICATIONS

Apfelbaum et al. Postoperative Pain Experience: Results from a National Survey Suggest Postoperative Pain Continues to Be Undermanaged. Anesth Analg 97:534-540 (2003).

Bley. Recent developments in transient receptor potential vanilloid receptor 1 agonist-based therapies. Expert Opin Investig Drugs. 13(11):1445-1456 (2004).

Caterina et al. The vanilloid receptor: a molecular gateway to the pain pathway. Annu Rev Neurosci. 24:487-517 (2001).

Chou et al. Management of Postoperative Pain: A Clinical Practice Guideline From the American Pain Society, the American Society of Regional Anesthesia and Pain Medicine, and the American Society of Anesthesiologists' Committee on Regional Anesthesia, Executive Committee, and Administrative Council. J Pain 17(2):131-157 (2016).

Gan et al. Incidence, patient satisfaction, and perceptions of post-surgical pain: results from a US national survey. Curr Med Res Opin 30(1):149-160 (2014).

Gomes et al. Cyclization-activated Prodrugs. Molecules 12:2484-2506 (2007).

Huang et al. Capsaicin and its analogues: structure-activity relationship study. Cur Med Chem 20:2661-2672 (2013).

Hunt et al. Disubstituted pyrimidines as Lck inhibitors. Bioorg Med Chem Lett. 19(18):5440-3 (2009).

Kehlet et al. Persistent postsurgical pain: risk factors and prevention. Lancet 367(9522):1618-1625 (2006).

Kirkpatrick et al. In vitro and in vivo assessment of the abuse potential of PF614, a novel BIO-MD™ prodrug of oxycodone. J Opiod Manag 13(1):39-49 (2017).

Liberman et al. Pharmaceutical Dosage Forms. 2nd Ed. 1:209-214 (1990).

Milewski et al. In vitro permeation of a pegylated naltrexone prodrug across microneedle-treated skin. J Control Release 146(1):37-44 (2010).

PCT/US2015/62531 International Search Report and Written Opinion dated Jan. 27, 2016.

PCT/US2017/034318 International Search Report and Written Opinion dated Aug. 23, 2017.

PCT/US2019/043517 International Search Report and Written Opinion dated Oct. 9, 2019.

PCT/US2019/043518 International Search Report and Written Opinion dated Oct. 24, 2019.

Pogatzki-Zahn et al. Room for improvement: unmet needs in postoperative pain management. Expert Rev. Neurother. 12(5):587-600 (2012).

Saari et al. Cyclization-activated prodrugs. Basic carbamates of 4-hydroxyanisole. J Med Chem 33(1):97-101 (1990).

Singh et al. Encyclopedia of Pharmaceutical Technology 2nd Ed. pp. 751-753 (2002).

Singh et al. Encyclopedia of Pharmaceutical Technology. 2nd Ed. pp. 754-757 (2002).

Stella et al. Prodrug strategies to overcome poor water solubility. Advanced Drug Delivery Reviews 59:677-694 (2007).

(56) References Cited

OTHER PUBLICATIONS

Swanson et al. Identification and biological evaluation of 4-(3-trifluoromethylpyridin-2-yl)piperazine-1-carboxylic acid (5-trifluoromethylpyridin-2-yl)amide, a high affinity TRPV1 (VR1) vanilloid receptor antagonist. J Med Chem 48(6):1857-1872 (2005).
U.S. Appl. No. 14/743,375 Office Action dated Jan. 22, 2016.
U.S. Appl. No. 15/529,076 Office Action dated Apr. 3, 2018.
U.S. Appl. No. 15/529,076 Office Action dated Jul. 11, 2019.
U.S. Appl. No. 15/529,076 Office Action dated Mar. 13, 2020.
U.S. Appl. No. 15/529,076 Office Action dated Oct. 29, 2018.
U.S. Appl. No. 16/303,082 Office Action dated Feb. 18, 2020.
U.S. Appl. No. 90/000,238 Supplemental Examination Certificate dated Nov. 15, 2017.
U.S. Appl. No. 96/000,238 Reasons For No Substantial New Question of Patentability dated Nov. 15, 2017.
Zawilska et al. Prodrugs: A challenge for the drug development. Pharmacological Reports 65:1-14 (2013).
U.S. Appl. No. 16/427,182 Office Action dated Dec. 30, 2020.
U.S. Appl. No. 16/427,182 Office Action dated Sep. 16, 2021.

\* cited by examiner

PRODRUGS OF PHENOLIC TRPV1 AGONISTS IN COMBINATION WITH LOCAL ANESTHETICS AND VASOCONSTRICTORS FOR IMPROVED LOCAL ANESTHESIA

CROSS-REFERENCE

This application is a continuation of U.S. application Ser. No. 16/303,082, filed on Nov. 19, 2018, which is a U.S. National Stage entry of PCT/US2017/034318 filed on May 24, 2017, which claims benefit of U.S. Provisional Application No. 62/341,529, filed on May 25, 2016, which are herein incorporated by reference in their entirety.

BACKGROUND OF THE INVENTION

More than 80% of patients who undergo surgical procedures experience acute postoperative pain and approximately 75% of those with postoperative pain report the severity as moderate, severe, or extreme (Apfelbaum et al., 2003; Gan et al., 2014). Evidence suggests that less than half of patients who undergo surgery report adequate postoperative pain relief (Apfelbaum et al., 2003). Inadequately controlled pain negatively affects quality of life, function, and functional recovery, the risk of post-surgical complications, and the risk of persistent postsurgical pain (Kehlet et al., 2006). Thus, there exists a need for medicaments with improved efficacy and longer duration of action for the treatment of pain.

SUMMARY OF THE INVENTION

In one aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), wherein the effective dose of Compound 1 is from about 0.01 mg to about 25 mg.

In another aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg and the effective dose of the local anesthetic is from about 0.5 mg to about 500 mg.

In another aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 µg to about 150 µg.

In another aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 150 µg.

In some embodiments of the methods described herein, the effective dose of the local anesthetic is from about 0.5 mg to about 250 mg. In some embodiments of the methods described herein, the effective dose of the local anesthetic is from about 1 mg to about 150 mg. In some embodiments of the methods described herein, the effective dose of the local anesthetic is from about 1 mg to about 75 mg. In some embodiments of the methods described herein, the effective dose of the local anesthetic is from about 1 mg to about 25 mg. In some embodiments of the methods described herein, the effective dose of the local anesthetic is from about 10 mg to about 75 mg. In some embodiments of the methods described herein, the effective dose of the vasoconstrictor is from about 1 µg to about 125 µg. In some embodiments of the methods described herein, the effective dose of the vasoconstrictor is from about 1 µg to about 100 µg. In some embodiments of the methods described herein, the effective dose of the vasoconstrictor is from about 1 µg to about 50 µg. In some embodiments of the methods described herein, the effective dose of the vasoconstrictor is from about 1 µg to about 25 µg. In some embodiments of the methods described herein, the effective dose of the vasoconstrictor is from about 5 µg to about 25 µg. In some embodiments of the methods described herein, the vasoconstrictor is epinephrine. In some embodiments of the methods described herein, the vasoconstrictor is phenylephrine. In some embodiments of the methods described herein, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments of the methods described herein, the local anesthetic is selected from the group consisting of bupivacaine, levobupivacaine, tetracaine, and ropivacaine. In some embodiments of the methods described herein, the local anesthetic is bupivacaine.

In another aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg.

In another aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 µg/mL to about 10 µg/mL, wherein the effective dose of Compound 1 is from about 0.01 mg to about 25 mg.

In another aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg.

In some embodiments of the methods described herein, the local anesthetic is in a concentration range from about 0.05% (0.5 mg/mL) to about 1% (10 mg/mL). In some embodiments of the methods described herein, the local anesthetic is in a concentration range from about 0.05% (0.5 mg/mL) to about 0.75% (7.5 mg/mL). In some embodiments of the methods described herein, the local anesthetic is in a concentration range from about 0.05% (0.5 mg/mL) to about 0.5% (5 mg/mL). In some embodiments of the methods described herein, the local anesthetic is in a concentration range from about 0.05% (0.5 mg/mL) to about 0.25% (2.5 mg/mL). In some embodiments of the methods described herein, the vasoconstrictor is in a concentration range from about 2 µg/mL to about 10 µg/mL. In some embodiments of the methods described herein, the vasoconstrictor is in a concentration range from about 2 µg/mL to about 5 µg/mL. In some embodiments of the methods described herein, the vasoconstrictor is epinephrine. In some embodiments of the methods described herein, the vasoconstrictor is phenylephrine. In some embodiments of the methods described herein, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments of the methods described herein, the local anesthetic is selected from the group consisting of bupivacaine, levobupivacaine, tetracaine, and ropivacaine. In some embodiments of the methods described herein, the local anesthetic is bupivacaine. In some embodiments of the methods described herein, the effective dose of Compound 1 is from about 0.01 mg to about 15 mg. In some embodiments of the methods described herein, the effective dose of Compound 1 is from about 0.1 mg to about 10 mg. In some embodiments of the methods described herein, the effective dose of Compound 1 is from about 0.5 mg to about 10 mg. In some embodiments of the methods described herein, the effective dose of Compound 1 is from about 0.5 mg to about 5 mg. In some embodiments of the methods described herein, the pain is post-surgical pain, post amputation pain, chronic post-surgical pain, and traumatic injury pain. In some embodiments of the methods described herein, the pain is post-surgical pain. In some embodiments of the methods described herein, the post-surgical pain is pain from a laparotomy, thoracotomy, thoraco-abdominal incision, flank incision, total hip replacement, total knee replacement, ACL reconstruction, rotator cuff repair, bunionectomy, laparoscopy, dental extraction, or open reduction internal fixation of fractures. In some embodiments of the methods described herein, the pain is traumatic injury pain. In some embodiments of the methods described herein, the traumatic injury pain is pain from a long bone, short bone, flat bone, or irregular bone fracture. In some embodiments of the methods described herein, the traumatic injury pain is pain from a hip or rib fracture. In some embodiments of the methods described herein, the pain is chronic post-surgical pain. In some embodiments of the methods described herein, the pain is chronic post-surgical pain after mastectomy or lumpectomy. In some embodiments of the methods described herein, the pain is chronic post-surgical pain after thoractomy. In some embodiments of the methods described herein, the pain is chronic post-surgical pain after amputation. In some embodiments of the methods described herein, the pain is chronic pain. In some embodiments of the methods described herein, the chronic pain is chronic pain associated with osteoarthritis. In some embodiments of the methods described herein, the chronic pain is chronic pain associated with osteoarthritis of the knee. In some embodiments of the methods described herein, the chronic pain is chronic musculoskeletal pain. In some embodiments of the methods described herein, the chronic pain is chronic musculoskeletal pain of the lower back. In some embodiments of the methods described herein, the effective dose is administered to the subject is in a dosing volume from about 1 mL to about 120 mL. In some embodiments of the methods described herein, the effective dose is administered to the subject is in a dosing volume from about 10 mL to about 30 mL. In some embodiments of the methods described herein, the effective dose is administered to the subject is in a dosing volume from about 30 mL to about 120 mL. In some embodiments of the methods described herein, the effective dose is administered to the subject is in a dosing volume from about 1 mL to about 10 mL. In some embodiments of the methods described herein, the subject is awake. In some embodiments of the methods described herein, the subject is sedated.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg, the effective dose of the vasoconstrictor is from about 1 µg to about 150 µg, and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg, the effective dose of the vasoconstrictor is from about 1 µg to about 150 µg, and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 µg to about 75 µg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 5 µg/mL, wherein the effective dose of Compound 1 is from about 0.01 mg to about 25 mg.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 µg/mL to about 10 µg/mL, wherein the effective dose of Compound 1 is from about 0.01 mg to about 25 mg and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 µg/mL to about 10 µg/mL, wherein the effective dose of Compound 1 is from about 0.01 mg to about 25 mg and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 10 µg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 5 µg/mL, wherein the effective dose of Compound 1 is from about 0.01 mg to about 25 mg.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 10 µg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 5 µg/mL, wherein the effective dose of Compound 1 is from about 0.01 mg to about 25 mg.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is bupivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is selected from the group consisting of bupivacaine, levobupivacaine, tetracaine, and ropivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is bupivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.75% (7.5 mg/mL), and a vasoconstrictor in a concentration range from about 1 µg/mL to about 10 µg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.5% (5 mg/mL), and a vasoconstrictor in a concentration range from about 1 µg/mL to about 10 µg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.25% (2.5 mg/mL), and a vasoconstrictor in a concentration range from about 1 µg/mL to about 10 µg/mL, wherein the effective dose of Compound 1 is from about 0.01 mg to about 25 mg.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien, and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, and ropivacaine, and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is bupivacaine, and the vasoconstrictor is epinephrine.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien, and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, and ropivacaine, and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is bupivacaine, and the vasoconstrictor is phenylephrine.

In some embodiments of the aforementioned embodiments, the effective dose of Compound 1 is from about 0.01 mg to about 15 mg. In some embodiments of the aforementioned embodiments, the effective dose of Compound 1 is from about 0.1 mg to about 10 mg. In some embodiments of the aforementioned embodiments, the effective dose of Compound 1 is from about 0.5 mg to about 10 mg. In some embodiments of the aforementioned embodiments, the effective dose of Compound 1 is from about 0.5 mg to about 5 mg. In some embodiments of the aforementioned embodiments is a method of treating or preventing pain in a subject in need thereof, wherein the pain is post-surgical pain, post amputation pain, chronic post-surgical pain, and traumatic injury pain. In some embodiments of the aforementioned embodiments is a method of treating or preventing pain in a subject in need thereof, wherein the pain is post-surgical pain. In some embodiments of the aforementioned embodiments is a method of treating or preventing pain in a subject in need thereof, wherein the post-surgical pain is pain from a laparotomy, thoracotomy, thoraco-abdominal incision, flank incision, total hip replacement, total knee replacement, ACL reconstruction, rotator cuff repair, bunionectomy, laparoscopy, dental extraction, or open reduction internal fixation of fractures. In some embodiments of the aforementioned embodiments is a method of treating or preventing pain in a subject in need thereof, wherein the pain is traumatic injury pain. In some embodiments of the aforementioned embodiments is a method of treating or preventing pain in a subject in need thereof, wherein the traumatic injury pain is pain from a hip or rib fracture. In some embodiments of the aforementioned embodiments is a method of treating or preventing pain in a subject in need thereof, wherein the pain is chronic post-surgical pain. In some embodiments of the aforementioned embodiments is a method of treating or preventing pain in a subject in need thereof, wherein the pain is chronic post-surgical pain after mastectomy or lumpectomy. In some embodiments of the aforementioned embodiments is a method of treating or preventing pain in a subject in need thereof, wherein the pain is chronic post-surgical pain after thoracotomy. In some embodiments of the aforementioned embodiments is a method of treating or preventing pain in a subject in need thereof, wherein the pain is chronic post-surgical pain after amputation. In some embodiments of the methods described herein, the pain is chronic pain. In some embodiments of the aforementioned embodiments is a method of treating or preventing pain in a subject in need thereof, wherein the chronic pain is chronic pain associated with osteoarthritis. In some embodiments of the aforementioned embodiments is a method of treating or preventing pain in a subject in need thereof, wherein the chronic pain is chronic pain associated with osteoarthritis of the knee. In some embodiments of the aforementioned embodiments is a method of treating or preventing pain in a subject in need thereof, wherein the chronic pain is chronic musculoskeletal pain. In some embodiments of the aforementioned embodiments is a method of treating or preventing pain in a subject in need thereof, wherein the chronic pain is chronic musculoskeletal pain of the lower back. In some embodiments of the aforementioned embodiments, the effective dose administered to the subject is in a dosing volume from about 1 mL to about 120 mL. In some embodiments of the aforementioned embodiments, the effective dose administered to the subject is in a dosing volume from about 10 mL to about 30 mL. In some embodiments of the aforementioned embodiments, the effective dose administered to the subject is in a dosing volume from about 30 mL to about 120 mL. In some embodiments of the aforementioned embodiments, the effective dose administered to the subject is in a dosing volume less than about 10 mL. In some embodiments of the aforementioned embodiments, the subject is awake. In some embodiments of the aforementioned embodiments, the subject is sedated.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a pharmaceutically acceptable carrier, wherein the effective dose of Compound 1 is from about 0.01 mg to about 25 mg.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a pharmaceutically acceptable carrier, wherein the effective dose of Compound 1 is from about 0.01 mg to about 25 mg and the effective dose of the local anesthetic is from about 0.5 mg to about 500 mg.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a vasoconstrictor, and a pharmaceutically acceptable carrier, wherein the effective dose of Compound 1 is from about 0.01 mg to about 25 mg and the effective dose of the vasoconstrictor is from about 1 µg to about 150 µg.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, a vasoconstrictor, and a pharmaceutically acceptable carrier, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 150 µg.

In some embodiments of the pharmaceutical compositions described herein, the effective dose of the local anesthetic is from about 0.5 mg to about 250 mg. In some embodiments of the pharmaceutical compositions described herein, the effective dose of the local anesthetic is from about 1 mg to about 150 mg. In some embodiments of the pharmaceutical compositions described herein, the effective dose of the local anesthetic is from about 1 mg to about 75 mg. In some embodiments of the pharmaceutical compositions described herein, the effective dose of the local anesthetic is from about 1 mg to about 25 mg. In some embodiments of the pharmaceutical compositions described herein, the effective dose of the local anesthetic is from about 10 mg to about 75 mg. In some embodiments of the pharmaceutical compositions described herein, the effective dose of the vasoconstrictor is from about 1 µg to about 125 µg. In some embodiments of the pharmaceutical compositions described herein, the effective dose of the vasoconstrictor is from about 1 µg to about 100 µg. In some embodiments of the pharmaceutical compositions described herein, the effective dose of the vasoconstrictor is from about 1 µg to about 50 µg. In some embodiments of the pharmaceutical compositions described herein, the effective dose of the vasoconstrictor is from about 1 µg to about 25 µg. In some embodiments of the pharmaceutical compositions described herein, the effective dose of the vasoconstrictor is from about 5 µg to about 25 µg. In some embodiments of the pharmaceutical compositions described herein, the vasoconstrictor is epinephrine. In some embodiments of the pharmaceutical compositions described herein, the vasoconstrictor is phenylephrine. In some embodiments of the pharmaceutical compositions described herein, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments of the pharmaceutical compositions described herein, the local anesthetic is selected from the group consisting of bupivacaine, levobupivacaine, tetracaine, and ropivacaine. In some embodiments of the pharmaceutical compositions described herein, the local anesthetic is bupivacaine.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a pharmaceutically acceptable carrier, wherein the effective dose of Compound 1 is from about 0.01 mg to about 25 mg.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a vasoconstrictor in a concentration range from about 1 µg/mL to about 10 µg/mL, and a pharmaceutically acceptable carrier, wherein the effective dose of Compound 1 is from about 0.01 mg to about 25 mg.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), a vasoconstrictor in a concentration range from about 1 µg/mL to about 10 µg/mL, and a pharmaceutically acceptable carrier, wherein the effective dose of Compound 1 is from about 0.01 mg to about 25 mg.

In some embodiments of the pharmaceutical compositions described herein, the local anesthetic is in a concentration range from about 0.05% (0.5 mg/mL) to about 1% (10 mg/mL). In some embodiments of the pharmaceutical compositions described herein, the local anesthetic is in a concentration range from about 0.05% (0.5 mg/mL) to about 0.75% (7.5 mg/mL). In some embodiments of the pharmaceutical compositions described herein, the local anesthetic is in a concentration range from about 0.05% (0.5 mg/mL) to about 0.5% (5 mg/mL). In some embodiments of the pharmaceutical compositions described herein, the local anesthetic is in a concentration range from about 0.05% (0.5 mg/mL) to about 0.25% (2.5 mg/mL). In some embodiments of the pharmaceutical compositions described herein, the vasoconstrictor is in a concentration range from about 2 µg/mL to about 10 µg/mL. In some embodiments of the pharmaceutical compositions described herein, the vasoconstrictor is in a concentration range from about 2 µg/mL to about 5 µg/mL. In some embodiments of the pharmaceutical compositions described herein, the vasoconstrictor is epinephrine. In some embodiments of the pharmaceutical compositions described herein, the vasoconstrictor is phenylephrine. In some embodiments of the pharmaceutical compositions described herein, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments of the pharmaceutical compositions described herein, the local anesthetic is selected from the group consisting of bupivacaine, levobupivacaine, tetracaine, and ropivacaine. In some embodiments of the pharmaceutical compositions described herein, the local anesthetic is bupivacaine. In some embodiments of the pharmaceutical compositions described herein, the effective dose of Compound 1 is from about 0.01 mg to about 15 mg. In some embodiments of the pharmaceutical compositions described herein, the effective dose of Compound 1 is from about 0.1 mg to about 10 mg. In some embodiments of the pharmaceutical compositions described herein, the effective dose of Compound 1 is from about 0.5 mg to about 10 mg. In some embodiments of the pharmaceutical compositions described herein, the effective dose of Compound 1 is from about 0.5 mg to about 5 mg. In some embodiments of the pharmaceutical compositions described herein, the pain is post-surgical pain, post amputation pain, chronic post-surgical pain, and traumatic injury pain. In some embodiments of the pharmaceutical compositions described herein, the pain is post-surgical pain. In some embodiments of the pharmaceutical compositions described herein, the post-surgical pain is pain from a laparotomy, thoracotomy, thoraco-abdominal incision, flank incision, total hip replacement, total knee replacement, ACL reconstruction, rotator cuff repair, bunionectomy, laparoscopy, dental extraction, or open reduction internal fixation of fractures. In some embodiments of the pharmaceutical compositions described herein, the pain is traumatic injury pain. In some embodiments of the pharmaceutical compositions described herein, the traumatic injury pain is pain from a long bone, short bone, flat bone, or irregular bone fracture. In some embodiments of the pharmaceutical compositions described herein, the traumatic injury pain is pain from a hip or rib fracture. In some embodiments of the pharmaceutical compositions described herein, the pain is chronic post-surgical pain. In some embodiments of the pharmaceutical compositions described herein, the pain is chronic post-surgical pain after mastectomy or lumpectomy. In some embodiments of the pharmaceutical compositions described herein, the pain is chronic post-surgical pain after thoractomy. In some embodiments of the pharmaceutical compositions described herein, the pain is chronic post-surgical pain after amputation. In some embodiments of the pharmaceutical compositions described herein, the pain is chronic pain. In some embodiments of the pharmaceutical compositions described herein, the chronic pain is chronic pain associated with osteoarthritis. In some embodiments of the pharmaceutical compositions described herein, the chronic pain is chronic pain associated with osteoarthritis of the knee. In some embodiments of the pharmaceutical compositions described herein, the chronic pain is chronic musculoskeletal pain. In some embodiments of the pharmaceutical compositions described herein, the chronic pain is chronic musculoskeletal pain of the lower back. In some embodiments of the pharmaceutical compositions described herein, the carrier is sterile water. In some embodiments of the pharmaceutical compositions described herein, the carrier is sterile saline. In some embodiments of the pharmaceutical compositions described herein, the effective dose is administered to the subject is in a dosing volume from about 1 mL to about 120 mL. In some embodiments of the pharmaceutical compositions described herein, the effective dose is administered to the subject is in a dosing volume from about 10 mL to about 30 mL. In some embodiments of the pharmaceutical compositions described herein, the effective dose is administered to the subject is in a dosing volume from about 30 mL to about 120 mL. In some embodiments of the pharmaceutical compositions described herein, the effective dose is administered to the subject is in a dosing volume from about 1 mL to about 10 mL.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 μg/mL to about 10 μg/mL, wherein the effective dose of Compound 1 is from about 0.01 mg to about 25 mg and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 μg/mL to about 10 μg/mL, wherein the effective dose of Compound 1 is from about 0.01 mg to about 25 mg and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 μg/mL to about 10 μg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 μg/mL to about 5 μg/mL, wherein the effective dose of Compound 1 is from about 0.01 mg to about 25 mg.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 μg/mL to about 10 μg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 μg/mL to about 5 μg/mL, wherein the effective dose of Compound 1 is from about 0.01 mg to about 25 mg.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)

piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is bupivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is selected from the group consisting of bupivacaine, levobupivacaine, tetracaine, and ropivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is bupivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.75% (7.5 mg/mL), and a vasoconstrictor in a concentration range from about 1 µg/mL to about 10 µg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.5% (5 mg/mL), and a vasoconstrictor in a concentration range from about 1 µg/mL to about 10 µg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.25% (2.5 mg/mL), and a vasoconstrictor in a concentration range from about 1 µg/mL to about 10 µg/mL, wherein the effective dose of Compound 1 is from about 0.01 mg to about 25 mg.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien, and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, and ropivacaine, and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg, the local anesthetic is bupivacaine, and the vasoconstrictor is epinephrine.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien, and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg, the local anesthetic is selected from the group consisting of bupivacaine, levobupivacaine, tetracaine, and ropivacaine, and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg, the local anesthetic is bupivacaine, and the vasoconstrictor is phenylephrine.

In some embodiments of the aforementioned embodiments, the effective dose of Compound 1 is from about 0.01 mg to about 15 mg. In some embodiments of the aforementioned embodiments, the effective dose of Compound 1 is from about 0.1 mg to about 10 mg. In some embodiments of the aforementioned embodiments, the effective dose of Compound 1 is from about 0.5 mg to about 10 mg. In some embodiments of the aforementioned embodiments, the effective dose of Compound 1 is from about 0.5 mg to about 5 mg. In some embodiments of the aforementioned embodiments is a pharmaceutical composition for the treatment or prevention of pain, wherein the pain is post-surgical pain, post amputation pain, chronic post-surgical pain, and traumatic injury pain. In some embodiments of the aforementioned embodiments is a pharmaceutical composition for the treatment or prevention of pain, wherein the pain is post-surgical pain. In some embodiments of the aforementioned embodiments is a pharmaceutical composition for the treatment or prevention of pain, wherein the post-surgical pain is pain from a laparotomy, thoracotomy, thoraco-abdominal incision, flank incision, total hip replacement, total knee replacement, ACL reconstruction, rotator cuff repair, bunionectomy, laparoscopy, dental extraction, or open reduction internal fixation of fractures. In some embodiments of the aforementioned embodiments is a pharmaceutical composition for the treatment or prevention of pain, wherein the pain is traumatic injury pain. In some embodiments of the aforementioned embodiments is a pharmaceutical composition for the treatment or prevention of pain, wherein the traumatic injury pain is pain from a hip or rib fracture. In some embodiments of the aforementioned embodiments is a pharmaceutical composition for the treatment or prevention of pain, wherein the pain is chronic post-surgical pain. In some embodiments of the aforementioned embodiments is a pharmaceutical composition for the treatment or prevention of pain, wherein the pain is chronic post-surgical pain after mastectomy or lumpectomy. In some embodiments of the aforementioned embodiments is a pharmaceutical composition for the treatment or prevention of pain, wherein the pain is chronic post-surgical pain after thoractomy. In some embodiments of the aforementioned embodiments is a pharmaceutical composition for the treatment or prevention of pain, wherein the pain is chronic post-surgical pain after amputation. In some embodiments of the aforementioned embodiments is a pharmaceutical composition for the treatment or prevention of pain, the pain is chronic pain. In some embodiments of the aforementioned embodiments is a pharmaceutical composition for the treatment or prevention of pain, wherein the chronic pain is chronic pain associated with osteoarthritis. In some embodiments of the aforementioned embodiments is a pharmaceutical composition for the treatment or prevention of pain, wherein the chronic pain is chronic pain associated with osteoarthritis of the knee. In some embodiments of the aforementioned embodiments, the carrier is sterile water. In some embodiments of the aforementioned embodiments, the carrier is sterile saline. In some embodiments of the aforementioned embodiments, the effective dose is in a dosing volume from about 1 mL to about 120 mL. In some embodiments of the aforementioned embodiments, the effective dose is in a dosing volume from about 10 mL to about 30 mL. In some embodiments of the aforementioned embodiments, the effective dose is in a dosing volume from about 30 mL to about 120 mL. In some embodiments of the aforementioned embodiments, the effective dose is in a dosing volume less than about 10 mL.

Figure 1:
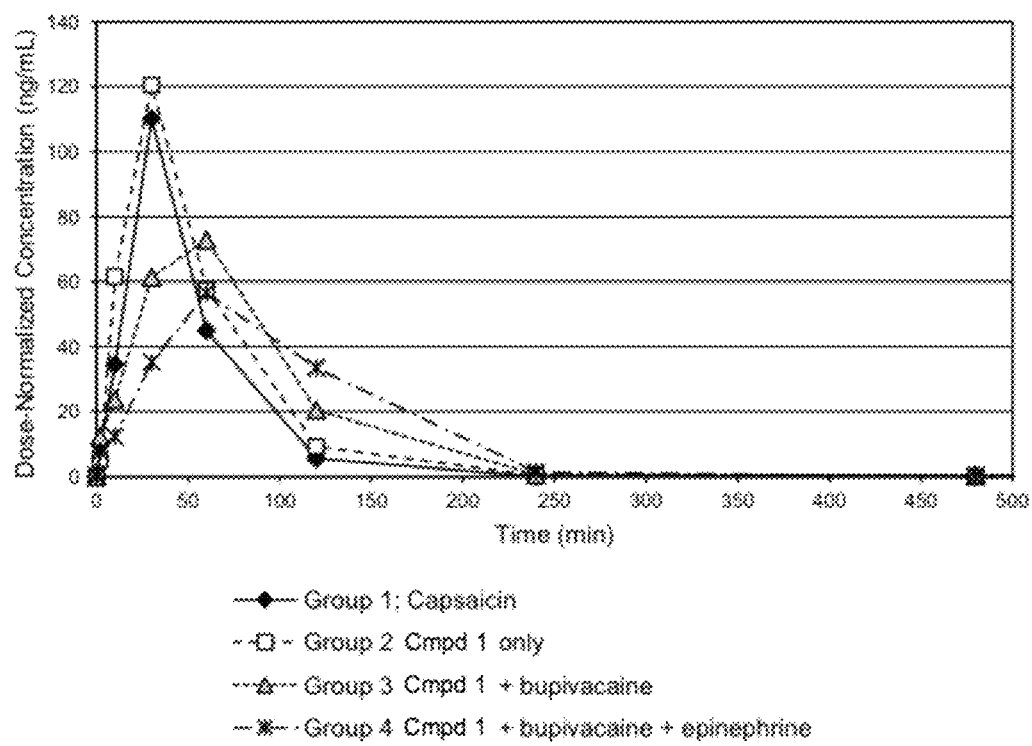
FIG. 1 shows the measurable whole blood concentrations of capsaicin vs. time following subcutaneous (SC) dosing in rats (linear plot). Group 1 (♦) represents the blood concentration of capsaicin following SC dosing of capsaicin (1.0 mg/kg) in 25% PEG300/sterile water. Group 2 (□) represents the blood concentration of capsaicin following SC dosing of Compound 1 HCl (at 1.62 mg/kg) in sterile water. Group 3 (Δ) represents the blood concentration of capsaicin following SC dosing of Compound 1 HCl (at 1.62 mg/kg) in 0.25% bupivacaine hydrochloride solution. Group 4 (*) represents the blood concentration of capsaicin following SC dosing of Compound 1 HCl (at 1.62 mg/kg) in 0.25% bupivacaine hydrochloride solution plus epinephrine (1:200, 000) solution).

Group 1. 0.5% Bupivacaine solution with epinephrine (1:200,000), 0.875 mg
Group 2. Capsaicin, 100 µg in 25% PEG300/saline (v/v)
Group 3. Capsaicin, 100 µg in 0.5% bupivacaine solution (in 25% PEG300, based on volume)
Group 4. Compound 1 HCl, 81 µg in 0.9% saline
Group 5. Compound 1 HCl, 81 µg in 0.5% bupivacaine solution
Group 6. Compound 1 HCl, 162 µg in 0.9% saline
Group 7. Compound 1 HCl, 162 µg in 0.5% bupivacaine solution
Group 8. Compound 1 HCl, 162 µg in 0.5% bupivacaine solution plus epinephrine (1:200,000)
Group 9. Compound 1 HCl, 243 µg in 0.5% bupivacaine solution plus epinephrine (1:200,000)
Group 10. Vehicle control (0.9% Saline)

DETAILED DESCRIPTION

Pain management in patients after surgery remains insufficient (Pogatzki-Zahn et al., 2012), and there is no ideal way to provide continuous, effective pain relief beyond 12-18 hours after surgery. Systemic pharmacological therapies remain the mainstay of postoperative pain relief, with opioids a key component, especially for moderate-to-severe pain. Systemic opioids are effective, but increase cost and morbidity, especially due to known safety issues such as respiratory depression, gastrointestinal dysfunction, and abuse. Non-opioid analgesics including acetaminophen, nonselective NSAIDs, and selective COX-2 inhibitors are useful for the treatment of light-to-moderate pain and are part of a balanced multimodal pain treatment (Pogatzki-Zahn et al., 2012). These products also have known safety risks. The use of peripheral regional anesthetic techniques have been shown to be effective as a component of multimodal analgesia for management of postoperative pain associated with a number of surgical procedures, including thoracotomy, lower extremity joint surgery, shoulder surgery, cesarean section, hemorrhoid surgery, and circumcision. It is recommended that clinicians should consider use of surgical site-specific or peripheral regional analgesic techniques in adults and children as part of multimodal analgesia, particularly in patients who undergo lower extremity and upper extremity surgical procedures (Chou et al., 2016).

Site-specific local anesthetic infiltration techniques in which local anesthetic is injected into the tissues around the surgical site are attractive as a component of multi-modal analgesia due to the potential for prevention of post-operative pain, with lower potential safety risks due to the local nature of administration. Treating pain at its source with local anesthetic is highly effective, but limited due to its typically short duration of action. Use of long-acting local anesthetics such as bupivacaine at the surgical site is recommended in the clinical practice guideline on the basis of evidence showing benefit for the surgical procedure in question (Chou et al., 2016). The use of subcutaneous and/or periarticular infiltration of long-acting local anesthetics at the surgical site has been shown to be effective as a component of multimodal analgesia in several surgical procedures, including total knee replacement, arthroscopic knee surgeries, cesarean section, laparotomy, and hemorrhoid surgery, although some studies showed no benefit (Chou et al., 2016).

The utility of conventional local anesthetics is limited by their relatively short duration of action (6-8 hours) and there is a clear need for longer lasting site-specific product whose duration of effect better matches the duration of pain after surgery. Exparel®, an extended release liposomal formulation of bupivacaine, is approved for single-dose infiltration into the surgical site to produce postsurgical analgesia. The analgesic benefit of Exparel® when compared to placebo, however, is limited to 12-24 hours. Moreover, there is limited data to support any benefit of Exparel® over standard bupivacaine.

An additional shortcoming of traditional local anesthetics is their nonselective effect on sensory and motor nerves. The blocking of pain conduction with conventional local anesthetics is accompanied by numbness and motor weakness. The extension of muscle weakness and numbness into the postoperative period would interfere with mobilization and rehabilitation. Another potential drawback is the risk of injury in the absence of sensation. Pain serves as protective reflex and an extended nonselective block of sensory function could result in injury to a numb region of the body Capsaicin, the main ingredient responsible for the hot pungent taste of chili peppers, is an alkaloid found in the Capsicum family. Capsaicin (8-methyl-N-vanillyl-6-nonenamide) is a highly selective agonist for transient receptor potential vanilloid 1 receptor (TRPV1; formerly known as vanilloid receptor 1 (VR1)), a ligand-gated, non-selective cation channel. TRPV1 is preferentially expressed on small-diameter sensory neurons, predominately on C-fibers and to a lesser extent A-delta fibers which specialize in the detection of painful or noxious sensations. TRPV1 responds to stimuli including capsaicin, heat, and extracellular acidification, and will integrate simultaneous exposures to these stimuli. (Caterina M J, Julius D. The vanilloid receptor: a molecular gateway to the pain pathway. *Annu Rev Neurosci*. 2001. 24:487-517).

TRPV1 agonists, such as capsaicin, have been shown to diminish pain in various settings, but there are problems associated with their use. The initial effects of the activation of TRPV1-expressing (capsaicin-sensitive) nociceptors include burning sensations, hyperalgesia, allodynia, and erythema. However, after prolonged exposure to low-concentration capsaicin or single exposures to high-concentration capsaicin or other TRPV1 agonists, the small-diameter sensory axons become less sensitive to a variety of stimuli, including capsaicin or thermal stimuli. Following the initial activation of nociceptors, capsaicin and other TRPV1 agonists induce a long-lasting, selective reduction in pain responses lasting days to weeks. These later-stage effects of capsaicin are frequently referred to as "desensitization" and are the rationale for the development of capsaicin formulations for the treatment of various pain syndromes and other conditions. (Bley, K. R. Recent developments in transient receptor potential vanilloid receptor 1 agonist-based therapies. *Expert Opin Investig Drugs.* 2004. 13(11): 1445-1456).

In contrast to TRPV1 agonists, local anesthetics produce their effects by blocking voltage-gated sodium channels and thus inhibiting axon conduction. Most commonly used local anesthetics bind at the intracellular site of the sodium channel and therefore must traverse the relatively hydrophobic lipid bilayer to exert its effect. Local anesthetics are only able to cross the lipid membrane in their deprotonated (freebase) form. Because most local anesthetics, at physiological pH, are only fractionally deprotonated, this limits the amount of local anesthetics that may cross the lipid bilayer. In contrast, the protonated form cannot readily cross the lipid membrane, will not gain access to the sodium-channel binding sites, and in-turn will not have analgesic effect. Upon reversibly binding to and inactivating sodium channels, local anesthetics produce anesthesia by inhibiting excitation of nerve endings or by blocking conduction in peripheral nerves. Sodium influx through these channels is necessary for the depolarization of nerve cell membranes and subsequent propagation of impulses along the course of the nerve.

For reasons described above, most commonly used local anesthetics are considered hydrophobic compounds that exert their action on the sodium channel via diffusion through a lipid bilayer. It has been demonstrated that sodium-channel blockers can be targeted into nociceptors by the application of TRPV1 agonists to produce a pain-specific local anaesthesia (Woolf, et al, Nature, 2007; 449: 607-11). These studies have shown that the co-administration of a local anesthetic and a TRPV1 agonist, produces significant decreases in the response to mechanical and thermal stimulation. Additionally, the regional anesthesia produced by this mechanism appears to be associated with less motor block than that seen with conventional local anesthesia using hydrophobic local anaesthetics.

Vasoconstrictor agents, with an emphasis on epinephrine, are frequently co-administered with local anesthetics to reduce the rate of systemic absorption of co-administered agents, which in turn increases the neural uptake and decreases the clearance of local anesthetic agents at the site of injection. Based on this effect, vasoconstrictors increase the efficacy of the local anesthetic agent due to a decreased rate of systemic absorption of the agent. Although the effects of vasoconstrictors are principally pharmacokinetic in nature, vasoconstrictors themselves can have antinociceptive effects and, when absorbed from the site of injection, vasoconstrictors may elicit cardiovascular effects able to alter the pharmacokinetics and effects of co-administered drugs. It has been suggested that the action of vasoconstrictors is likely influenced by a variety of aspects such as hydrophobicity of the co-administered drug, the tissue and blood flow at the site of administration, the dosing vehicle, and the amount of the drugs given. Additionally, the extent which vasoconstrictors limit the system absorption of local anesthetic is dependent on the type, dose, and concentration of local anesthetic and of the nature of the site of injection. The peak blood levels (Cmax) of local anesthetics were decreased via the co-administration of epinephrine in addition to a delay in Tmax of the local anesthetics.

In some embodiments described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic. In some embodiments described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor. In some embodiments described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor.

In some embodiments described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic. In some embodiments described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor. In some embodiments described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor.

In some embodiments, the methods and pharmaceutical compositions described herein provide pain relief for multiple days, following a single injection.

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications, and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included," is not limiting.

The section headings used herein are for organizational purposes only and are not to be construed as limiting the subject matter described.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, and compositions described herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, and swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition (e.g., arresting the development of the disease or condition), relieving the disease or condition, causing regression of the disease or condition, relieving a condition caused by the disease or condition, or stopping the symptoms of the disease or condition either prophylactically and/or therapeutically.

As used herein, amelioration of the symptoms of a particular disease, disorder, or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, a modulator can cause an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

The term "acceptable" with respect to a formulation, composition or ingredient, as used herein, means having no persistent detrimental effect on the general health of the subject being treated.

By "pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that one active ingredient, e.g compound described herein, and a co-agent, are both administered to a patient simultaneously in the form of a single entity or dosage. The term "non-fixed combination" means that one active ingredient, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the pharmaceutical composition that includes a compound described herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "co-administration" or the like, as used herein, are meant to encompass administration of the selected therapeutic agents to a single patient, and are intended to include treatment regimens in which the agents are administered by the same or different route of administration or at the same or different time.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds.

"Bioavailability" refers to the percentage of the weight of the compound disclosed herein that is delivered into the general circulation of the animal or human being studied. The total exposure (AUC(0-∞)) of a drug when administered intravenously is usually defined as 100% bioavailable (F %). "Oral bioavailability" refers to the extent to which a compound disclosed herein, is absorbed into the general circulation when the pharmaceutical composition is taken orally as compared to intravenous injection.

"Blood plasma concentration" refers to the concentration of a compound disclosed herein, in the plasma component of blood of a subject. It is understood that the plasma concentration of compounds described herein may vary significantly between subjects, due to variability with respect to metabolism and/or possible interactions with other therapeutic agents. In accordance with one embodiment disclosed herein, the blood plasma concentration of the compounds disclosed herein may vary from subject to subject. Likewise, values such as maximum plasma concentration (Cmax) or time to reach maximum plasma concentration (Tmax), or total area under the plasma concentration time curve (AUC (0-∞)) may vary from subject to subject. Due to this variability, the amount necessary to constitute "a therapeutically effective amount" of a compound may vary from subject to subject.

"Blood concentration" refers to the concentration of a compound disclosed herein, in the blood of a subject. It is understood that the blood concentration of compounds described herein may vary significantly between subjects, due to variability with respect to metabolism and/or possible interactions with other therapeutic agents. In accordance with one embodiment disclosed herein, the blood concentration of the compounds disclosed herein may vary from subject to subject. Likewise, values such as maximum blood concentration (Cmax) or time to reach maximum blood concentration (Tmax), or total area under the blood concentration time curve ($AUC_{(0-\infty)}$) may vary from subject to subject. Due to this variability, the amount necessary to constitute "a therapeutically effective amount" of a compound may vary from subject to subject.

Compound 1

The chemical structure of Compound 1 ((E)-2-methoxy-4-((8-methylnon-6-enamido)methyl)phenyl 2-((methylamino)methyl)piperidine-1-carboxylate hydrochloride) is shown below:

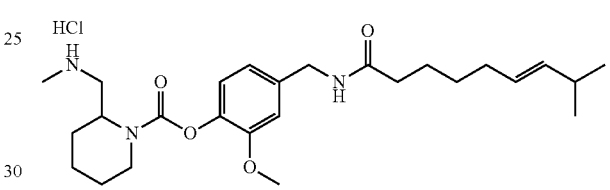

Compound 1 releases capsaicin and cyclic urea Compound 2 (2-methylhexahydroimidazo[1,5-a]pyridin-3(2H)-one) under well-defined rates via a pH driven, intra-molecular cyclization release reaction after Compound 1 has been delivered to the body and/or is exposed to specific physiological conditions:

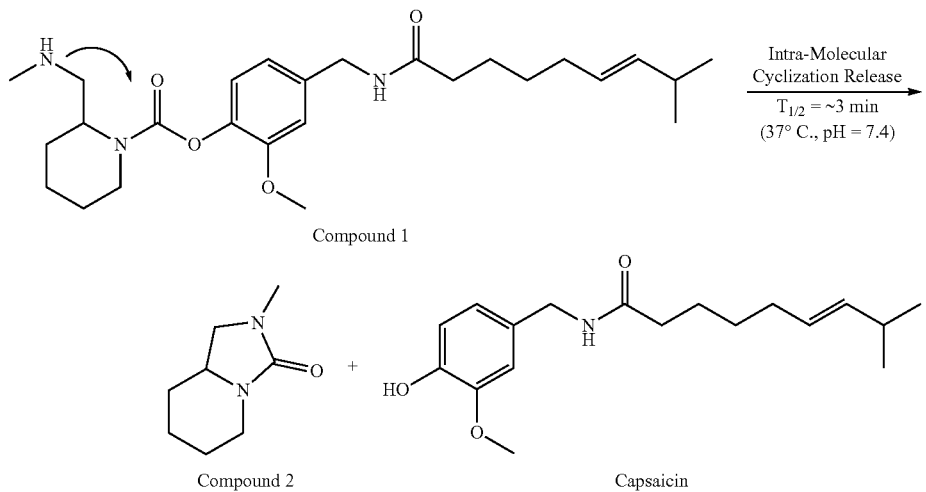

In some embodiments, the chemical-release kinetics of Compound 1 to capsaicin imparts two desirable properties: (a) reduced and/or delayed pungency due to the avoidance of the rapid delivery of a bolus dose of capsaicin and (b) tuning of specific pharmacological activity/results.

In addition, Compound 1 has significantly higher hydrophilicity/water solubility than capsaicin and, hence, is better able to be incorporated into commonly used aqueous formulations. The improved water solubility of Compound 1 is significant when co-delivering other medications, especially when administering multiple sterile agents via injection.

In some embodiments, Compound 1 eliminates the reliance on special requirements for formulations or delivery devices for capsaicin in order to 1) accommodate the very low water solubility of capsaicin and 2) reduce the acute pungency associated with the administration of capsaicin.

In some embodiments, the rate at which Compound 1 releases capsaicin is modified by the addition of buffers. In some embodiments, the addition of a buffer provides a time window where turnover to capsaicin is significantly delayed until the return of physiological pH.

Compound Synthesis

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics. In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein.

Local Anesthetics

The term "local anesthetic" means a drug which provides local pain relief. On average, these drugs average six to ten hours of pain relief when given in different sites and for different types of surgery. For many types of surgery, it would be preferable to have durations of pain relief that last two to five days or more.

In some embodiments described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic. In some embodiments described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor. In some embodiments described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic. In some embodiments described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor.

In some embodiments of the methods and pharmaceutical compositions described herein, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments of the methods and pharmaceutical compositions described herein, the local anesthetic is bupivacaine. In some embodiments of the methods and pharmaceutical compositions described herein, the local anesthetic is levobupivacaine. In some embodiments of the methods and pharmaceutical compositions described herein, the local anesthetic is tetracaine. In some embodiments of the methods and pharmaceutical compositions described herein, the local anesthetic is ropivacaine. In some embodiments of the methods and pharmaceutical compositions described herein, the local anesthetic is lidocaine. In some embodiments of the methods and pharmaceutical compositions described herein, the local anesthetic is prilocaine. In some embodiments of the methods and pharmaceutical compositions described herein, the local anesthetic is mepivacaine. In some embodiments of the methods and pharmaceutical compositions described herein, the local anesthetic is procaine. In some embodiments of the methods and pharmaceutical compositions described herein, the local anesthetic is chloroprocaine. In some embodiments of the methods and pharmaceutical compositions described herein, the local anesthetic is propoxycaine. In some embodiments of the methods and pharmaceutical compositions described herein, the local anesthetic is hexylcaine. In some embodiments of the methods and pharmaceutical compositions described herein, the local anesthetic is cyclomethycaine. In some embodiments of the methods and pharmaceutical compositions described herein, the local anesthetic is benoxinate. In some embodiments of the methods and pharmaceutical compositions described herein, the local anesthetic is butacaine. In some embodiments of the methods and pharmaceutical compositions described herein, the local anesthetic is proparacaine. In some embodiments of the methods and pharmaceutical compositions described herein, the local anesthetic is cocaine. In some embodiments of the methods and pharmaceutical compositions described herein, the local anesthetic is phenacaine. In some embodiments of the methods and pharmaceutical compositions described herein, the local anesthetic is dibucaine. In some embodiments of the methods and pharmaceutical compositions described herein, the local anesthetic is falicaine. In some embodiments of the methods and pharmaceutical compositions described herein, the local anesthetic is dyclonine. In some embodiments of the methods and pharmaceutical compositions described herein, the local anesthetic is spramoxine. In some embodiments of the methods and pharmaceutical compositions described herein, the local anesthetic is dimethisoquien.

Vasoconstrictors

The term vasoconstrictor refers to compounds acting locally to restrict blood flow, and thereby retain the co-administered agents at the site in which they are injected. The use of vasoconstrictors affords substantially decreasing systemic toxicity of the co-administered agent. In some embodiments, the vasoconstrictors are those acting on alpha adrenergic receptors. In some embodiments, the vasoconstrictor is epinephrine. In some embodiments, the vasoconstrictor is phenylephrine.

In some embodiments described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor. In some embodiments described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor. In some embodiments described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor. In some embodiments described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor.

In some embodiments of the methods and pharmaceutical compositions described herein, the vasoconstrictor is epinephrine or phenylephrine. In some embodiments of the methods and pharmaceutical compositions described herein, the vasoconstrictor is epinephrine. In some embodiments of the methods and pharmaceutical compositions described herein, the vasoconstrictor is phenylephrine.

Methods

In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), wherein the effective dose of Compound 1 is from about 0.01 mg to about 25 mg.

In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg and the effective dose of the local anesthetic is from about 0.5 mg to about 500 mg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg and the effective dose of the local anesthetic is from about 0.5 mg to about 250 mg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg and the effective dose of the local anesthetic is from about 1 mg to about 150 mg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg and the effective dose of the local anesthetic is from about 1 mg to about 75 mg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg and the effective dose of the local anesthetic is from about 1 mg to about 25 mg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg and the effective dose of the local anesthetic is from about 10 mg to about 75 mg. In some embodiments, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments, the local anesthetic is selected from the group consisting of bupivacaine, levobupivacaine, tetracaine, and ropivacaine. In some embodiments, the local anesthetic is bupivacaine.

In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 µg to about 150 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 µg to about 125 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 µg to about 100 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 µg to about 75 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 µg to about 50 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 µg to about 25 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 5 µg to about 25 µg. In some embodiments, the vasoconstrictor is epinephrine. In some embodiments, the vasoconstrictor is phenylephrine.

In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 150 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 250 mg, and the effective dose of the vasoconstrictor is from about 1 µg to about 150 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 150 mg, and the effective dose of the vasoconstrictor is from about 1 µg to about 150 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 75 mg, and the effective dose of the vasoconstrictor is from about 1 µg to about 150 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 25 mg, and the effective dose of the vasoconstrictor is from about 1 µg to about 150 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 10 mg to about 75 mg, and the effective dose of the vasoconstrictor is from about 10 µg to about 150 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 125 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 100 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 50 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 25 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 5 µg to about 25 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 250 mg, and the effective dose of the vasoconstrictor is from about 1 µg to about 100 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 150 mg, and the effective dose of the vasoconstrictor is from about 1 µg to about 100 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 250 mg, and the effective dose of the vasoconstrictor is from about 1 µg to about 50 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 150 mg, and the effective dose of the vasoconstrictor is from about 1 µg to about 50 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 75 mg, and the effective dose of the vasoconstrictor is from about 1 µg to about 100 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 25 mg, and the effective dose of the vasoconstrictor is from about 1 µg to about 100 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 25 mg, and the effective dose of the vasoconstrictor is from about 1 µg to about 50 µg. In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 25 mg, and the effective dose of the vasoconstrictor is from about 1 µg to about 25 µg. In some embodiments, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien; and the vasoconstrictor is epinephrine. In some embodiments, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien; and the vasoconstrictor is phenylephrine. In some embodiments, the local anesthetic is selected from the group consisting of bupivacaine, levobupivacaine, tetracaine, and ropivacaine; and the vasoconstrictor is epinephrine. In some embodiments, the local anesthetic is selected from the group consisting of bupivacaine, levobupivacaine, tetracaine, and ropivacaine; and the vasoconstrictor is phenylephrine. In some embodiments, the local anesthetic is bupivacaine and the vasoconstrictor is epinephrine. In some embodiments, the local anesthetic is bupivacaine and the vasoconstrictor is phenylephrine.

In some embodiments, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg.

In another aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 μg/mL to about 10 μg/mL, wherein the effective dose of Compound 1 is from about 0.01 mg to about 25 mg.

In another aspect, described herein is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 μg/mL to about 10 μg/mL, wherein the effective dose of Compound 1 is from about 0.01 mg to about 25 mg and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 μg/mL to about 10 μg/mL, wherein the effective dose of Compound 1 is from about 0.01 mg to about 25 mg and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 μg/mL to about 10 μg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 μg/mL to about 10 μg/mL, wherein the effective dose of Compound 1 is from about 0.01 mg to about 25 mg and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 μg/mL to about 10 μg/mL, wherein the effective dose of Compound 1 is from about 0.01 mg to about 25 mg and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 μg/mL to about 5 μg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 μg/mL to about 5 μg/mL, wherein the effective dose of Compound 1 is from about 0.01 mg to about 25 mg and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 μg/mL to about 5 μg/mL, wherein the effective dose of Compound 1 is from about 0.01 mg to about 25 mg and the vasoconstrictor is phenylephrine.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 μg/mL to about 10 μg/mL, wherein the effective dose of Compound 1 is from about 0.01 mg to about 25 mg and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 μg/mL to about 10 μg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 10 µg/mL, wherein the effective dose of Compound 1 is from about 0.01 mg to about 25 mg and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 10 µg/mL, wherein the effective dose of Compound 1 is from about 0.01 mg to about 25 mg and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 5 µg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 5 µg/mL, wherein the effective dose of Compound 1 is from about 0.01 mg to about 25 mg and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 5 µg/mL, wherein the effective dose of Compound 1 is from about 0.01 mg to about 25 mg and the vasoconstrictor is phenylephrine.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is bupivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.1% (10 mg/mL), wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.1% (10 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.1% (10 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.1% (10 mg/mL), wherein the effective dose of Compound 1 is from about 0.01 mg to about 25 mg and the local anesthetic is bupivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg and the local anesthetic is bupivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg and the local anesthetic is bupivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg and the local anesthetic is bupivacaine.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is selected from the group consisting of bupivacaine, levobupivacaine, tetracaine, and ropivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is bupivacaine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.75% (7.5 mg/mL), and a vasoconstrictor in a concentration range from about 1 µg/mL to about 10 µg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.5% (5 mg/mL), and a vasoconstrictor in a concentration range from about 1 µg/mL to about 10 µg/mL, wherein the effective dose of Compound 1 is from about 0.01 mg to about 25 mg. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.25% (2.5 mg/mL), and a vasoconstrictor in a concentration range from about 1 µg/mL to about 10 µg/mL, wherein the effective dose of Compound 1 is from about 0.01 mg to about 25 mg.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien, and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, and ropivacaine, and the vasoconstrictor is epinephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is bupivacaine, and the vasoconstrictor is epinephrine.

In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien, and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, and ropivacaine, and the vasoconstrictor is phenylephrine. In some embodiments is a method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1- carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is bupivacaine, and the vasoconstrictor is phenylephrine.

In some embodiments of the aforementioned methods, the effective dose of Compound 1 is from about 0.01 mg to about 300 mg. In some embodiments of the aforementioned methods, the effective dose of Compound 1 is from about 0.01 mg to about 250 mg. In some embodiments of the aforementioned methods, the effective dose of Compound 1 is from about 0.01 mg to about 200 mg. In some embodiments of the aforementioned methods, the effective dose of Compound 1 is from about 0.01 mg to about 150 mg. In some embodiments of the aforementioned methods, the effective dose of Compound 1 is from about 0.01 mg to about 100 mg. In some embodiments of the aforementioned methods, the effective dose of Compound 1 is from about 0.01 mg to about 50 mg. In some embodiments of the aforementioned methods, the effective dose of Compound 1 is from about 0.01 mg to about 30 mg. In some embodiments of the aforementioned methods, the effective dose of Compound 1 is from about 0.01 mg to about 25 mg. In some embodiments of the aforementioned methods, the effective dose of Compound 1 is from about 0.01 mg to about 20 mg. In some embodiments of the aforementioned methods, the effective dose of Compound 1 is from about 0.01 mg to about 15 mg. In some embodiments of the aforementioned methods, the effective dose of Compound 1 is from about 0.01 mg to about 14 mg. In some embodiments of the aforementioned methods, the effective dose of Compound 1 is from about 0.01 mg to about 13 mg. In some embodiments of the aforementioned methods, the effective dose of Compound 1 is from about 0.01 mg to about 12 mg. In some embodiments of the aforementioned methods, the effective dose of Compound 1 is from about 0.01 mg to about 11 mg. In some embodiments of the aforementioned methods, the effective dose of Compound 1 is from about 0.01 mg to about 10 mg. In some embodiments of the aforementioned methods, the effective dose of Compound 1 is from about 0.01 mg to about 9 mg. In some embodiments of the aforementioned methods, the effective dose of Compound 1 is from about 0.01 mg to about 8 mg. In some embodiments of the aforementioned methods, the effective dose of Compound 1 is from about 0.01 mg to about 7 mg. In some embodiments of the aforementioned methods, the effective dose of Compound 1 is from about 0.01 mg to about 6 mg. In some embodiments of the aforementioned methods, the effective dose of Compound 1 is from about 0.01 mg to about 5 mg. In some embodiments of the aforementioned methods, the effective dose of Compound 1 is from about 0.01 mg to about 4 mg. In some embodiments of the aforementioned methods, the effective dose of Compound 1 is from about 0.01 mg to about 3 mg. In some embodiments of the aforementioned methods, the effective dose of Compound 1 is from about 0.01 mg to about 2 mg. In some embodiments of the aforementioned methods, the effective dose of Compound 1 is from about 0.01 mg to about 1 mg. In some embodiments of the aforementioned methods, the effective dose of Compound 1 is from about 0.01 mg to about 0.5 mg. In some embodiments of the aforementioned methods, the effective dose of Compound 1 is from about 0.1 mg to about 10 mg. In some embodiments of the aforementioned methods, the effective dose of Compound 1 is from about 0.1 mg to about 25 mg. In some embodiments of the aforementioned methods, the effective dose of Compound 1 is from about 0.1 mg to about 20 mg. In some embodiments of the aforementioned methods, the effective dose of Compound 1 is from about 0.1 mg to about 15 mg. In some embodiments of the aforementioned methods, the effective dose of Compound 1 is from about 0.1 mg to about 10 mg. In some embodiments of the aforementioned methods, the effective dose of Compound 1 is from about 0.1 mg to about 5 mg. In some embodiments of the aforementioned methods, the effective dose of Compound 1 is from about 0.5 mg to about 25 mg. In some embodiments of the aforementioned methods, the effective dose of Compound 1 is from about 0.5 mg to about 20 mg. In some embodiments of the aforementioned methods, the effective dose of Compound 1 is from about 0.5 mg to about 15 mg. In some embodiments of the aforementioned methods, the effective dose of Compound 1 is from about 0.5 mg to about 10 mg. In some embodiments of the aforementioned methods, the effective dose of Compound 1 is from about 0.5 mg to about 5 mg. In some embodiments of the aforementioned methods, the effective dose of Compound 1 is from about 1 mg to about 100 mg. In some embodiments of the aforementioned methods, the effective dose of Compound 1 is from about 1 mg to about 50 mg. In some embodiments of the aforementioned methods, the effective dose of Compound 1 is about 0.01 mg, about 0.05 mg, about 0.1 mg, about 0.25 mg, about 0.5 mg, about 0.75 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, or about 25 mg, including increments therein.

In some embodiments of the aforementioned methods, the effective dose of the local anesthetic is from about 0.01 mg to about 600 mg. In some embodiments of the aforementioned methods, the effective dose of the local anesthetic is from about 0.5 mg to about 500 mg. In some embodiments of the aforementioned methods, the effective dose of the local anesthetic is from about 0.5 mg to about 400 mg. In some embodiments of the aforementioned methods, the effective dose of the local anesthetic is from about 0.5 mg to about 300 mg. In some embodiments of the aforementioned methods, the effective dose of the local anesthetic is from about 0.5 mg to about 250 mg. In some embodiments of the aforementioned methods, the effective dose of the local anesthetic is from about 0.5 mg to about 200 mg. In some embodiments of the aforementioned methods, the effective dose of the local anesthetic is from about 0.5 mg to about 150 mg. In some embodiments of the aforementioned methods, the effective dose of the local anesthetic is from about 1 mg to about 150 mg. In some embodiments of the aforementioned methods, the effective dose of the local anesthetic is from about 1 mg to about 100 mg. In some embodiments of the aforementioned methods, the effective dose of the local anesthetic is from about 1 mg to about 75 mg. In some embodiments of the aforementioned methods, the effective dose of the local anesthetic is from about 1 mg to about 50 mg. In some embodiments of the aforementioned methods, the effective dose of the local anesthetic is from about 1 mg to about 40 mg. In some embodiments of the aforementioned methods, the effective dose of the local anesthetic is from about 1 mg to about 30 mg. In some embodiments of the aforementioned methods, the effective dose of the local anesthetic is from about 1 mg to about 25 mg. In some embodiments of the aforementioned methods, the effective dose of the local anesthetic is from about 10 mg to about 500 mg. In some embodiments of the aforementioned methods, the effective dose of the local anesthetic is from about 10 mg to about 250 mg. In some embodiments of the aforementioned methods, the effective dose of the local anesthetic is from about 10 mg to about 200 mg. In some embodiments of the aforementioned methods, the effective dose of the local anesthetic is from about 10 mg to about 150 mg. In some embodiments of the aforementioned methods, the effective dose of the local anesthetic is from about 10 mg to about 100 mg. In some embodiments of the aforementioned methods, the effective dose of the local anesthetic is from about 10 mg to about 75 mg. In some embodiments of the aforementioned methods, the effective dose of the local anesthetic is from about 10 mg to about 50 mg.

In some embodiments of the aforementioned methods, the local anesthetic is in a concentration range from about 0.05% (0.5 mg/mL) to about 1.8% (18 mg/mL). In some embodiments of the aforementioned methods, the local anesthetic is in a concentration range from about 0.05% (0.5 mg/mL) to about 1.6% (16 mg/mL). In some embodiments of the aforementioned methods, the local anesthetic is in a concentration range from about 0.05% (0.5 mg/mL) to about 1.4% (14 mg/mL). In some embodiments of the aforementioned methods, the local anesthetic is in a concentration range from about 0.05% (0.5 mg/mL) to about 1.2% (12 mg/mL). In some embodiments of the aforementioned methods, the local anesthetic is in a concentration range from about 0.05% (0.5 mg/mL) to about 1.0% (10 mg/mL). In some embodiments of the aforementioned methods, the local anesthetic is in a concentration range from about 0.05% (0.5 mg/mL) to about 0.9% (9 mg/mL). In some embodiments of the aforementioned methods, the local anesthetic is in a concentration range from about 0.05% (0.5 mg/mL) to about 0.8% (8 mg/mL). In some embodiments of the aforementioned methods, the local anesthetic is in a concentration range from about 0.05% (0.5 mg/mL) to about 0.7% (7 mg/mL). In some embodiments of the aforementioned methods, the local anesthetic is in a concentration range from about 0.05% (0.5 mg/mL) to about 0.6% (6 mg/mL). In some embodiments of the aforementioned methods, the local anesthetic is in a concentration range from about 0.05% (0.5 mg/mL) to about 0.5% (5 mg/mL). In some embodiments of the aforementioned methods, the local anesthetic is in a concentration range from about 0.05% (0.5 mg/mL) to about 0.4% (4 mg/mL). In some embodiments of the aforementioned methods, the local anesthetic is in a concentration range from about 0.05% (0.5 mg/mL) to about 0.3% (3 mg/mL). In some embodiments of the aforementioned methods, the local anesthetic is in a concentration range from about 0.05% (0.5 mg/mL) to about 0.25% (2.5 mg/mL). In some embodiments of the aforementioned methods, the local anesthetic is in a concentration range from about 0.05% (0.5 mg/mL) to about 0.2% (2 mg/mL). In some embodiments of the aforementioned methods, the local anesthetic is in a concentration range from about 0.05% (0.5 mg/mL) to about 0.15% (1.5 mg/mL). In some embodiments of the aforementioned methods, the local anesthetic is in a concentration range from about 0.05% (0.5 mg/mL) to about 0.1% (1 mg/mL). In some embodiments of the aforementioned methods, the local anesthetic is in a concentration range from about 0.1% (1 mg/mL) to about 1.0% (10 mg/mL). In some embodiments of the aforementioned methods, the local anesthetic is in a concentration range from about 0.1% (1 mg/mL) to about 0.5% (5 mg/mL). In some embodiments of the aforementioned methods, the local anesthetic is in a concentration range from about 0.1% (1 mg/mL) to about 0.25% (2.5 mg/mL).

In some embodiments of the aforementioned methods, the effective dose of the vasoconstrictor is from about 0.1 µg to about 300 µg. In some embodiments of the aforementioned methods, the effective dose of the vasoconstrictor is from about 0.1 µg to about 250 µg. In some embodiments of the aforementioned methods, the effective dose of the vasoconstrictor is from about 0.1 µg to about 200 µg. In some embodiments of the aforementioned methods, the effective dose of the vasoconstrictor is from about 0.1 µg to about 150 µg. In some embodiments of the aforementioned methods, the effective dose of the vasoconstrictor is from about 0.5 µg to about 150 µg. In some embodiments of the aforementioned methods, the effective dose of the vasoconstrictor is from about 1 µg to about 150 µg. In some embodiments of the aforementioned methods, the effective dose of the vasoconstrictor is from about 1 µg to about 125 µg. In some embodiments of the aforementioned methods, the effective dose of the vasoconstrictor is from about 1 µg to about 100 µg. In some embodiments of the aforementioned methods, the effective dose of the vasoconstrictor is from about 1 µg to about 90 µg. In some embodiments of the aforementioned methods, the effective dose of the vasoconstrictor is from about 1 µg to about 75 µg. In some embodiments of the aforementioned methods, the effective dose of the vasoconstrictor is from about 1 µg to about 60 µg. In some embodiments of the aforementioned methods, the effective dose of the vasoconstrictor is from about 1 µg to about 60 µg. In some embodiments of the aforementioned methods, the effective dose of the vasoconstrictor is from about 1 µg to about 50 µg. In some embodiments of the aforementioned methods, the effective dose of the vasoconstrictor is from about 1 µg to about 40 µg. In some embodiments of the aforementioned methods, the effective dose of the vasoconstrictor is from about 1 µg to about 30 µg. In some embodiments of the aforementioned methods, the effective dose of the vasoconstrictor is from 1 µg to about 25 µg. In some embodiments of the aforementioned methods, the effective dose of the vasoconstrictor is from about 1 µg to about 20 µg. In some embodiments of the aforementioned methods, the effective dose of the vasoconstrictor is from about 1 µg to about 15 µg. In some embodiments of the aforementioned methods, the effective dose of the vasoconstrictor is from about 1 µg to about 10 µg. In some 1 µg to about 5 µg. In some embodiments of the aforementioned methods, the effective dose of the vasoconstrictor is from about 10 µg to about 150 µg. In some embodiments of the aforementioned methods, the effective dose of the vasoconstrictor is from about 10 µg to about 125 µg. In some embodiments of the aforementioned methods, the effective dose of the vasoconstrictor is from about 10 µg to about 100 µg. In some embodiments of the aforementioned methods, the effective dose of the vasoconstrictor is from about 10 µg to about 75 µg. In some embodiments of the aforementioned methods, the effective dose of the vasoconstrictor is from about 10 µg to about 50 µg.

In some embodiments of the aforementioned methods, the vasoconstrictor is in a concentration range from about 2 µg/mL to about 10 µg/mL. In some embodiments of the aforementioned methods, the vasoconstrictor is in a concentration range from about 2 µg/mL to about 5 µg/mL. In some embodiments of the aforementioned methods, the concentration of the vasoconstrictor is about 10 µg/mL. In some embodiments of the aforementioned methods, the concentration of the vasoconstrictor is about 9 µg/mL. In some embodiments of the aforementioned methods, the concentration of the vasoconstrictor is about 8 µg/mL. In some embodiments of the aforementioned methods, the concentration of the vasoconstrictor is about 7 µg/mL. In some embodiments of the aforementioned methods, the concentration of the vasoconstrictor is about 6 µg/mL. In some embodiments of the aforementioned methods, the concentration of the vasoconstrictor is about 5 µg/mL. In some embodiments of the aforementioned methods, the concentration of the vasoconstrictor is about 4 µg/mL. In some embodiments of the aforementioned methods, the concentration of the vasoconstrictor is about 3 µg/mL. In some embodiments of the aforementioned methods, the concentration of the vasoconstrictor is about 2 µg/mL. In some embodiments of the aforementioned methods, the concentration of the vasoconstrictor is about 1 µg/mL.

In some embodiments of the aforementioned methods is a method of treating or preventing pain in a subject in need thereof, wherein the pain is post-surgical pain, post amputation pain, chronic post-surgical pain, and traumatic injury pain. In some embodiments of the aforementioned methods is a method of treating or preventing pain in a subject in need thereof, wherein the pain is post-surgical pain. In some embodiments of the aforementioned methods is a method of treating or preventing pain in a subject in need thereof, wherein the post-surgical pain is pain from a laparotomy, thoracotomy, thoraco-abdominal incision, flank incision, total hip replacement, total knee replacement, ACL reconstruction, rotator cuff repair, bunionectomy, laparoscopy, dental extraction, or open reduction internal fixation of fractures. In some embodiments of the aforementioned methods is a method of treating or preventing pain in a subject in need thereof, wherein the post-surgical pain is pain from a laparotomy. In some embodiments of the aforementioned methods is a method of treating or preventing pain in a subject in need thereof, wherein the post-surgical pain is pain from a thoracotomy. In some embodiments of the aforementioned methods is a method of treating or preventing pain in a subject in need thereof, wherein the post-surgical pain is pain from a thoraco-abdominal incision. In some embodiments of the aforementioned methods is a method of treating or preventing pain in a subject in need thereof, wherein the post-surgical pain is pain from a flank incision. In some embodiments of the aforementioned methods is a method of treating or preventing pain in a subject in need thereof, wherein the post-surgical pain is pain from a total hip replacement. In some embodiments of the aforementioned methods is a method of treating or preventing pain in a subject in need thereof, wherein the post-surgical pain is pain from a total knee replacement. In some embodiments of the aforementioned methods is a method of treating or preventing pain in a subject in need thereof, wherein the post-surgical pain is pain from an ACL reconstruction. In some embodiments of the aforementioned methods is a method of treating or preventing pain in a subject in need thereof, wherein the post-surgical pain is pain from a rotator cuff repair. In some embodiments of the aforementioned methods is a method of treating or preventing pain in a subject in need thereof, wherein the post-surgical pain is pain from a bunionectomy. In some embodiments of the aforementioned methods is a method of treating or preventing pain in a subject in need thereof, wherein the post-surgical pain is pain from a laparoscopy. In some embodiments of the aforementioned methods is a method of treating or preventing pain in a subject in need thereof, wherein the post-surgical pain is pain from a dental extraction. In some embodiments of the aforementioned methods is a method of treating or preventing pain in a subject in need thereof, wherein the post-surgical pain is pain from an open reduction internal fixation of fractures. In some embodiments of the aforementioned methods is a method of treating or preventing pain in a subject in need thereof, wherein the pain is post amputation pain. In some embodiments of the aforementioned methods is a method of treating or preventing pain in a subject in need thereof, wherein the pain is chronic post-surgical pain. In some embodiments of the aforementioned methods is a method of treating or preventing pain in a subject in need thereof, wherein the pain is chronic post-surgical pain after mastectomy or lumpectomy referred to as "post mastectomy syndrome". In some embodiments of the aforementioned methods is a method of treating or preventing pain in a subject in need thereof, wherein the pain is chronic post-surgical pain after thoracotomy. In some embodiments of the aforementioned methods is a method of treating or preventing pain in a subject in need thereof, wherein the pain is chronic post-surgical pain after amputation referred to as "stump pain". In some embodiments of the aforementioned methods is a method of treating or preventing pain in a subject in need thereof, wherein the pain is traumatic injury pain. In some embodiments of the aforementioned methods is a method of treating or preventing pain in a subject in need thereof, wherein the pain is traumatic injury pain from a long bone, short bone, flat bone, or irregular bone fracture. In some embodiments of the aforementioned methods is a method of treating or preventing pain in a subject in need thereof, wherein the pain is traumatic injury pain from a long bone fracture. In some embodiments of the aforementioned methods is a method of treating or preventing pain in a subject in need thereof, wherein the pain is traumatic injury pain from a short bone fracture. In some embodiments of the aforementioned methods is a method of treating or preventing pain in a subject in need thereof, wherein the pain is traumatic injury pain from a flat bone fracture. In some embodiments of the aforementioned methods is a method of treating or preventing pain in a subject in need thereof, wherein the pain is traumatic injury pain from an irregular bone fracture. In some embodiments of the aforementioned methods is a method of treating or preventing pain in a subject in need thereof, wherein the traumatic injury pain is pain from a hip or rib fracture. In some embodiments of the aforementioned methods is a method of treating or preventing pain in a subject in need thereof, wherein the traumatic injury pain is pain from a hip fracture. In some embodiments of the aforementioned methods is a method of treating or preventing pain in a subject in need thereof, wherein the traumatic injury pain is pain from a rib fracture.

In some embodiments of the aforementioned methods is a method of treating or preventing pain in a subject in need thereof, wherein the pain is chronic pain. In some embodiments of the aforementioned methods is a method of treating or preventing pain in a subject in need thereof, wherein the pain is chronic pain associated with osteoarthritis. In some embodiments of the aforementioned methods is a method of treating or preventing pain in a subject in need thereof, wherein the pain is chronic pain associated with osteoarthritis of the knee. In some embodiments of the aforementioned methods is a method of treating or preventing pain in a subject in need thereof, wherein the pain is chronic musculoskeletal pain. In some embodiments of the aforementioned methods is a method of treating or preventing pain in a subject in need thereof, wherein the pain is musculoskeletal pain of the lower back.

In some embodiments of the aforementioned methods, the effective dose administered to the subject is in a dosing volume from about 1 mL to about 120 mL. In some embodiments of the aforementioned methods, the effective dose administered to the subject is in a dosing volume from about 5 mL to about 120 mL. In some embodiments of the aforementioned methods, the effective dose administered to the subject is in a dosing volume from about 10 mL to about 120 mL. In some embodiments of the aforementioned methods, the effective dose administered to the subject is in a dosing volume from about 10 mL to about 110 mL. In some embodiments of the aforementioned methods, the effective dose administered to the subject is in a dosing volume from about 10 mL to about 100 mL. In some embodiments of the aforementioned methods, the effective dose administered to the subject is in a dosing volume from about 10 mL to about 90 mL. In some embodiments of the aforementioned methods, the effective dose administered to the subject is in a dosing volume from about 10 mL to about 80 mL. In some embodiments of the aforementioned methods, the effective dose administered to the subject is in a dosing volume from about 10 mL to about 70 mL. In some embodiments of the aforementioned methods, the effective dose administered to the subject is in a dosing volume from about 10 mL to about 60 mL. In some embodiments of the aforementioned methods, the effective dose administered to the subject is in a dosing volume from about 10 mL to about 50 mL. In some embodiments of the aforementioned methods, the effective dose administered to the subject is in a dosing volume from about 10 mL to about 40 mL. In some embodiments of the aforementioned methods, the effective dose administered to the subject is in a dosing volume from about 10 mL to about 30 mL. In some embodiments of the aforementioned methods, the effective dose administered to the subject is in a dosing volume from about 10 mL to about 25 mL. In some embodiments of the aforementioned methods, the effective dose administered to the subject is in a dosing volume from about 10 mL to about 30 mL. In some embodiments of the aforementioned methods, the effective dose administered to the subject is in a dosing volume from about 30 mL to about 120 mL. In some embodiments of the aforementioned methods, the effective dose administered to the subject is in a dosing volume from about 30 mL to about 100 mL. In some embodiments of the aforementioned methods, the effective dose administered to the subject is in a dosing volume from about 30 mL to about 90 mL. In some embodiments of the aforementioned methods, the effective dose administered to the subject is in a dosing volume from about 30 mL to about 80 mL. In some embodiments of the aforementioned methods, the effective dose administered to the subject is in a dosing volume from about 1 mL to about 100 mL. In some embodiments of the aforementioned methods, the effective dose administered to the subject is in a dosing volume from about 1 mL to about 75 mL. In some embodiments of the aforementioned methods, the effective dose administered to the subject is in a dosing volume from about 1 mL to about 50 mL. In some embodiments of the aforementioned methods, the effective dose administered to the subject is in a dosing volume from about 1 mL to about 25 mL. In some embodiments of the aforementioned methods, the effective dose administered to the subject is in a dosing volume from about 1 mL to about 15 mL. In some embodiments of the aforementioned methods, the effective dose administered to the subject is in a dosing volume from about 1 mL to about 10 mL. In some embodiments of the aforementioned methods, the effective dose administered to the subject is in a dosing volume of about 10 mL. In some embodiments of the aforementioned methods, the effective dose administered to the subject is in a dosing volume of about 8 mL. In some embodiments of the aforementioned methods, the effective dose administered to the subject is in a dosing volume of about 6 mL. In some embodiments of the aforementioned methods, the effective dose administered to the subject is in a dosing volume of about 5 mL. In some embodiments of the aforementioned methods, the effective dose administered to the subject is in a dosing volume of about 4 mL. In some embodiments of the aforementioned methods, the effective dose administered to the subject is in a dosing volume of about 3 mL. In some embodiments of the aforementioned methods, the effective dose administered to the subject is in a dosing volume of about 2 mL. In some embodiments of the aforementioned methods, the effective dose administered to the subject is in a dosing volume of about 1 mL.

In some embodiments of the aforementioned methods, the subject is awake. In some embodiments of the aforementioned methods, the subject is sedated.

Pharmaceutical Compositions and Methods of Administration

In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), wherein the effective dose of Compound 1 is from about 0.01 mg to about 25 mg.

In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg and the effective dose of the local anesthetic is from about 0.5 mg to about 500 mg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg, the effective dose of the local anesthetic is from about 0.5 mg to about 250 mg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg, the effective dose of the local anesthetic is from about 1 mg to about 150 mg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg, the effective dose of the local anesthetic is from about 1 mg to about 75 mg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg, the effective dose of the local anesthetic is from about 1 mg to about 25 mg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a local anesthetic, wherein the effective dose of Compound 1 is from about 0.01 mg to about 25 mg, the effective dose of the local anesthetic is from about 10 mg to about 75 mg. In some embodiments, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments, the local anesthetic is selected from the group consisting of bupivacaine, levobupivacaine, tetracaine, and ropivacaine. In some embodiments, the local anesthetic is bupivacaine.

In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 μg to about 150 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 μg to about 125 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 μg to about 100 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 μg to about 75 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 μg to about 50 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 1 μg to about 25 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1) and a vasoconstrictor, wherein the effective dose of Compound 1 is from about 0.01 mg to about 25 mg and the effective dose of the vasoconstrictor is from about 5 μg to about 25 μg. In some embodiments, the vasoconstrictor is epinephrine. In some embodiments, the vasoconstrictor is phenylephrine.

In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 μg to about 150 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 250 mg, and the effective dose of the vasoconstrictor is from about 1 μg to about 150 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 150 mg, and the effective dose of the vasoconstrictor is from about 1 μg to about 150 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 75 mg, and the effective dose of the vasoconstrictor is from about 1 μg to about 150 μg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 25 mg, and the effective dose of the vasoconstrictor is from about 1 µg to about 150 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 10 mg to about 75 mg, and the effective dose of the vasoconstrictor is from about 10 µg to about 150 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 125 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 100 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 50 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 1 µg to about 25 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 500 mg, and the effective dose of the vasoconstrictor is from about 5 µg to about 25 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 250 mg, and the effective dose of the vasoconstrictor is from about 1 µg to about 100 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 150 mg, and the effective dose of the vasoconstrictor is from about 1 µg to about 100 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 0.5 mg to about 250 mg, and the effective dose of the vasoconstrictor is from about 1 µg to about 50 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 150 mg, and the effective dose of the vasoconstrictor is from about 1 µg to about 50 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 75 mg, and the effective dose of the vasoconstrictor is from about 1 µg to about 100 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 25 mg, and the effective dose of the vasoconstrictor is from about 1 µg to about 100 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 25 mg, and the effective dose of the vasoconstrictor is from about 1 µg to about 50 µg. In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic, and a vasoconstrictor, wherein the effective dose of Compound 1 is from about 0.01 mg to about 25 mg, the effective dose of the local anesthetic is from about 1 mg to about 25 mg, and the effective dose of the vasoconstrictor is from about 1 µg to about 25 µg. In some embodiments, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien; and the vasoconstrictor is epinephrine. In some embodiments, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien; and the vasoconstrictor is phenylephrine. In some embodiments, the local anesthetic is selected from the group consisting of bupivacaine, levobupivacaine, tetracaine, and ropivacaine; and the vasoconstrictor is epinephrine. In some embodiments, the local anesthetic is selected from the group consisting of bupivacaine, levobupivacaine, tetracaine, and ropivacaine; and the vasoconstrictor is phenylephrine. In some embodiments, the local anesthetic is bupivacaine and the vasoconstrictor is epinephrine. In some embodiments, the local anesthetic is bupivacaine and the vasoconstrictor is phenylephrine.

In some embodiments, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 µg/mL to about 10 µg/mL, wherein the effective dose of Compound 1 is from about 0.01 mg to about 25 mg.

In another aspect, described herein is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 µg/mL to about 10 µg/mL, wherein the effective dose of Compound 1 is from about 0.01 mg to about 25 mg and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 1 µg/mL to about 10 µg/mL, wherein the effective dose of Compound 1 is from about 0.01 mg to about 25 mg and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 10 µg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 10 µg/mL, wherein the effective dose of Compound 1 is from about 0.01 mg to about 25 mg and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 10 µg/mL, wherein the effective dose of Compound 1 is from about 0.01 mg to about 25 mg and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 5 µg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 5 µg/mL, wherein the effective dose of Compound 1 is from about 0.01 mg to about 25 mg and the vasoconstrictor is epinephrine. In some embodiments is a pharmaceutical composition for the treatment or prevention of pain, wherein the pharmaceutical composition comprises an effective dose of (E)-

2-methoxy-4-((8-methylnon-6-enamido)methyl)phenyl 2-((methylamino)methyl)piperidine-1-carboxylate hydrochloride (Compound 1), and a vasoconstrictor in a concentration range from about 2 µg/mL to about 5 µg/mL, wherein the effective dose of Compound 1 is from about 0.01 mg to about 25 mg and the vasoconstrictor is phenylephrine.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 10 µg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 10 µg/mL, wherein the effective dose of Compound 1 is from about 0.01 mg to about 25 mg and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 10 µg/mL, wherein the effective dose of Compound 1 is from about 0.01 mg to about 25 mg and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 5 µg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 5 µg/mL, wherein the effective dose of Compound 1 is from about 0.01 mg to about 25 mg and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 2 µg/mL to about 5 µg/mL, wherein the effective dose of Compound 1 is from about 0.01 mg to about 25 mg and the vasoconstrictor is phenylephrine.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 2% (20 mg/mL), wherein the effective dose of Compound 1 is from about 0.01 mg to about 25 mg and the local anesthetic is bupivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.1% (10 mg/mL), wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.1% (10 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.1% (10 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.1% (10 mg/mL), wherein the effective dose of Compound 1 is from about 0.01 mg to about 25 mg and the local anesthetic is bupivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.75% (7.5 mg/mL), wherein the effective dose of Compound 1 is from about 0.01 mg to about 25 mg and the local anesthetic is bupivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.5% (5 mg/mL), wherein the effective dose of Compound 1 is from about 0.01 mg to about 25 mg and the local anesthetic is bupivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg and the local anesthetic is selected from the group consisting of bupivacaine, levobupivacaine, tetracaine, and ropivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), and a local anesthetic in a concentration range from about 0.05% (0.5 mg/mL) to about 0.25% (2.5 mg/mL), wherein the effective dose of Compound 1 is from about 0.01 mg to about 25 mg and the local anesthetic is bupivacaine.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is selected from the group consisting of bupivacaine, levobupivacaine, tetracaine, and ropivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg and the local anesthetic is bupivacaine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.75% (7.5 mg/mL), and a vasoconstrictor in a concentration range from about 1 µg/mL to about 10 µg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.5% (5 mg/mL), and a vasoconstrictor in a concentration range from about 1 µg/mL to about 10 µg/mL, wherein the effective dose of Compound 1 is from about 0.01 mg to about 25 mg. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 0.25% (2.5 mg/mL), and a vasoconstrictor in a concentration range from about 1 µg/mL to about 10 µg/mL, wherein the effective dose of Compound 1 is from about 0.01 mg to about 25 mg.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien, and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, and ropivacaine, and the vasoconstrictor is epinephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is bupivacaine, and the vasoconstrictor is epinephrine.

In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, ropivacaine, lidocaine, prilocaine, mepivacaine, procaine, chloroprocaine, propoxycaine, hexylcaine, cyclomethycaine, benoxinate, butacaine, proparacaine, cocaine, phenacaine, dibucaine, falicaine, dyclonine, pramoxine, and dimethisoquien, and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is selected from the group consisting of bupivacaine, levobupivacaine, tetracaine, and ropivacaine, and the vasoconstrictor is phenylephrine. In some embodiments is a pharmaceutical composition for the treatment or prevention of pain, wherein the pharmaceutical composition comprises an effective dose of (E)-2-methoxy-4-((8-methylnon-6-enamido)methyl)phenyl 2-((methylamino)methyl)piperidine-1-carboxylate hydrochloride (Compound 1), a local anesthetic in a concentration range from about 0.05% (0.5 mg/mL) to about 2% (20 mg/mL), and a vasoconstrictor in a concentration range from about 1 µg/mL to about 10 µg/mL, wherein the effective dose of Compound 1 is from about 0.01 mg to about 25 mg, the local anesthetic is bupivacaine, and the vasoconstrictor is phenylephrine.

In some embodiments of the aforementioned pharmaceutical compositions, the effective dose of Compound 1 is from about 0.01 mg to about 300 mg. In some embodiments of the aforementioned pharmaceutical compositions, the effective dose of Compound 1 is from about 0.01 mg to about 250 mg. In some embodiments of the aforementioned pharmaceutical compositions, the effective dose of Compound 1 is from about 0.01 mg to about 200 mg. In some embodiments of the aforementioned pharmaceutical compositions, the effective dose of Compound 1 is from about 0.01 mg to about 150 mg. In some embodiments of the aforementioned pharmaceutical compositions, the effective dose of Compound 1 is from about 0.01 mg to about 100 mg. In some embodiments of the aforementioned pharmaceutical compositions, the effective dose of Compound 1 is from about 0.01 mg to about 50 mg. In some embodiments of the aforementioned pharmaceutical compositions, the effective dose of Compound 1 is from about 0.01 mg to about 30 mg. In some embodiments of the aforementioned pharmaceutical compositions, the effective dose of Compound 1 is from about 0.01 mg to about 25 mg. In some embodiments of the aforementioned pharmaceutical compositions, the effective dose of Compound 1 is from about 0.01 mg to about 20 mg. In some embodiments of the aforementioned pharmaceutical compositions, the effective dose of Compound 1 is from about 0.01 mg to about 15 mg. In some embodiments of the aforementioned pharmaceutical compositions, the effective dose of Compound 1 is from about 0.01 mg to about 14 mg. In some embodiments of the aforementioned pharmaceutical compositions, the effective dose of Compound 1 is from about 0.01 mg to about 13 mg. In some embodiments of the aforementioned pharmaceutical compositions, the effective dose of Compound 1 is from about 0.01 mg to about 12 mg. In some embodiments of the aforementioned pharmaceutical compositions, the effective dose of Compound 1 is from about 0.01 mg to about 11 mg. In some embodiments of the aforementioned pharmaceutical compositions, the effective dose of Compound 1 is from about 0.01 mg to about 10 mg. In some embodiments of the aforementioned pharmaceutical compositions, the effective dose of Compound 1 is from about 0.01 mg to about 9 mg. In some embodiments of the aforementioned pharmaceutical compositions, the effective dose of Compound 1 is from about 0.01 mg to about 8 mg. In some embodiments of the aforementioned pharmaceutical compositions, the effective dose of Compound 1 is from about 0.01 mg to about 7 mg. In some embodiments of the aforementioned pharmaceutical compositions, the effective dose of Compound 1 is from about 0.01 mg to about 6 mg. In some embodiments of the aforementioned pharmaceutical compositions, the effective dose of Compound 1 is from about 0.01 mg to about 5 mg. In some embodiments of the aforementioned pharmaceutical compositions, the effective dose of Compound 1 is from about 0.01 mg to about 4 mg. In some embodiments of the aforementioned pharmaceutical compositions, the effective dose of Compound 1 is from about 0.01 mg to about 3 mg. In some embodiments of the aforementioned pharmaceutical compositions, the effective dose of Compound 1 is from about 0.01 mg to about 2 mg. In some embodiments of the aforementioned pharmaceutical compositions, the effective dose of Compound 1 is from about 0.01 mg to about 1 mg. In some embodiments of the aforementioned pharmaceutical compositions, the effective dose of Compound 1 is from about 0.01 mg to about 0.5 mg. In some embodiments of the aforementioned pharmaceutical compositions, the effective dose of Compound 1 is from about 0.1 mg to about 10 mg. In some embodiments of the aforementioned pharmaceutical compositions, the effective dose of Compound 1 is from about 0.1 mg to about 25 mg. In some embodiments of the aforementioned pharmaceutical compositions, the effective dose of Compound 1 is from about 0.1 mg to about 20 mg. In some embodiments of the aforementioned pharmaceutical compositions, the effective dose of Compound 1 is from about 0.1 mg to about 15 mg. In some embodiments of the aforementioned pharmaceutical compositions, the effective dose of Compound 1 is from about 0.1 mg to about 10 mg. In some embodiments of the aforementioned pharmaceutical compositions, the effective dose of Compound 1 is from about 0.1 mg to about 5 mg. In some embodiments of the aforementioned pharmaceutical compositions, the effective dose of Compound 1 is from about 0.5 mg to about 25 mg. In some embodiments of the aforementioned pharmaceutical compositions, the effective dose of Compound 1 is from about 0.5 mg to about 20 mg. In some embodiments of the aforementioned pharmaceutical compositions, the effective dose of Compound 1 is from about 0.5 mg to about 15 mg. In some embodiments of the aforementioned pharmaceutical compositions, the effective dose of Compound 1 is from about 0.5 mg to about 10 mg. In some embodiments of the aforementioned pharmaceutical compositions, the effective dose of Compound 1 is from about 0.5 mg to about 5 mg. In some embodiments of the aforementioned pharmaceutical compositions, the effective dose of Compound 1 is from about 1 mg to about 100 mg. In some embodiments of the aforementioned pharmaceutical compositions, the effective dose of Compound 1 is from about 1 mg to about 50 mg. In some embodiments of the aforementioned pharmaceutical compositions, the effective dose of Compound 1 is about 0.01 mg, about 0.05 mg, about 0.1 mg, about 0.25 mg, about 0.5 mg, about 0.75 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, or about 25 mg, including increments therein.

In some embodiments of the aforementioned pharmaceutical compositions, the effective dose of the local anesthetic is from about 0.01 mg to about 600 mg. In some embodiments of the aforementioned pharmaceutical compositions, the effective dose of the local anesthetic is from about 0.5 mg to about 500 mg. In some embodiments of the aforementioned pharmaceutical compositions, the effective dose of the local anesthetic is from about 0.5 mg to about 400 mg. In some embodiments of the aforementioned pharmaceutical compositions, the effective dose of the local anesthetic is from about 0.5 mg to about 300 mg. In some embodiments of the aforementioned pharmaceutical compositions, the effective dose of the local anesthetic is from about 0.5 mg to about 250 mg. In some embodiments of the aforementioned pharmaceutical compositions, the effective dose of the local anesthetic is from about 0.5 mg to about 200 mg. In some embodiments of the aforementioned pharmaceutical compositions, the effective dose of the local anesthetic is from about 0.5 mg to about 150 mg. In some embodiments of the aforementioned pharmaceutical compositions, the effective dose of the local anesthetic is from about 1 mg to about 150 mg. In some embodiments of the aforementioned pharmaceutical compositions, the effective dose of the local anesthetic is from about 1 mg to about 100 mg. In some embodiments of the aforementioned pharmaceutical compositions, the effective dose of the local anesthetic is from about 1 mg to about 75 mg. In some embodiments of the aforementioned pharmaceutical compositions, the effective dose of the local anesthetic is from about 1 mg to about 50 mg. In some embodiments of the aforementioned pharmaceutical compositions, the effective dose of the local anesthetic is from about 1 mg to about 40 mg. In some embodiments of the aforementioned pharmaceutical compositions, the effective dose of the local anesthetic is from about 1 mg to about 30 mg. In some embodiments of the aforementioned pharmaceutical compositions, the effective dose of the local anesthetic is from about 1 mg to about 25 mg. In some embodiments of the aforementioned pharmaceutical compositions, the effective dose of the local anesthetic is from about 10 mg to about 500 mg. In some embodiments of the aforementioned pharmaceutical compositions, the effective dose of the local anesthetic is from about 10 mg to about 250 mg. In some embodiments of the aforementioned pharmaceutical compositions, the effective dose of the local anesthetic is from about 10 mg to about 200 mg. In some embodiments of the aforementioned pharmaceutical compositions, the effective dose of the local anesthetic is from about 10 mg to about 150 mg. In some embodiments of the aforementioned pharmaceutical compositions, the effective dose of the local anesthetic is from about 10 mg to about 100 mg. In some embodiments of the aforementioned pharmaceutical compositions, the effective dose of the local anesthetic is from about 10 mg to about 75 mg. In some embodiments of the aforementioned pharmaceutical compositions, the effective dose of the local anesthetic is from about 10 mg to about 50 mg.

In some embodiments of the aforementioned pharmaceutical compositions, the local anesthetic is in a concentration range from about 0.05% (0.5 mg/mL) to about 1.8% (18 mg/mL). In some embodiments of the aforementioned pharmaceutical compositions, the local anesthetic is in a concentration range from about 0.05% (0.5 mg/mL) to about 1.6% (16 mg/mL). In some embodiments of the aforementioned pharmaceutical compositions, the local anesthetic is in a concentration range from about 0.05% (0.5 mg/mL) to about 1.4% (14 mg/mL). In some embodiments of the aforementioned pharmaceutical compositions, the local anesthetic is in a concentration range from about 0.05% (0.5 mg/mL) to about 1.2% (12 mg/mL). In some embodiments of the aforementioned pharmaceutical compositions, the local anesthetic is in a concentration range from about 0.05% (0.5 mg/mL) to about 1.0% (10 mg/mL). In some embodiments of the aforementioned pharmaceutical compositions, the local anesthetic is in a concentration range from about 0.05% (0.5 mg/mL) to about 0.9% (9 mg/mL). In some embodiments of the aforementioned pharmaceutical compositions, the local anesthetic is in a concentration range from about 0.05% (0.5 mg/mL) to about 0.8% (8 mg/mL). In some embodiments of the aforementioned pharmaceutical compositions, the local anesthetic is in a concentration range from about 0.05% (0.5 mg/mL) to about 0.7% (7 mg/mL). In some embodiments of the aforementioned pharmaceutical compositions, the local anesthetic is in a concentration range from about 0.05% (0.5 mg/mL) to about 0.6% (6 mg/mL). In some embodiments of the aforementioned pharmaceutical compositions, the local anesthetic is in a concentration range from about 0.05% (0.5 mg/mL) to about 0.5% (5 mg/mL). In some embodiments of the aforementioned pharmaceutical compositions, the local anesthetic is in a concentration range from about 0.05% (0.5 mg/mL) to about 0.4% (4 mg/mL). In some embodiments of the aforementioned pharmaceutical compositions, the local anesthetic is in a concentration range from about 0.05% (0.5 mg/mL) to about 0.3% (3 mg/mL). In some embodiments of the aforementioned pharmaceutical compositions, the local anesthetic is in a concentration range from about 0.05% (0.5 mg/mL) to about 0.25% (2.5 mg/mL). In some embodiments of the aforementioned pharmaceutical compositions, the local anesthetic is in a concentration range from about 0.05% (0.5 mg/mL) to about 0.2% (2 mg/mL). In some embodiments of the aforementioned pharmaceutical compositions, the local anesthetic is in a concentration range from about 0.05% (0.5 mg/mL) to about 0.15% (1.5 mg/mL). In some embodiments of the aforementioned pharmaceutical compositions, the local anesthetic is in a concentration range from about 0.05% (0.5 mg/mL) to about 0.1% (1 mg/mL). In some embodiments of the aforementioned pharmaceutical compositions, the local anesthetic is in a concentration range from about 0.1% (1 mg/mL) to about 1.0% (10 mg/mL). In some embodiments of the aforementioned pharmaceutical compositions, the local anesthetic is in a concentration range from about 0.1% (1 mg/mL) to about 0.5% (5 mg/mL). In some embodiments of the aforementioned pharmaceutical compositions, the local anesthetic is in a concentration range from about 0.1% (1 mg/mL) to about 0.25% (2.5 mg/mL).

In some embodiments of the aforementioned pharmaceutical compositions, the effective dose of the vasoconstrictor is from about 0.1 µg to about 300 µg. In some embodiments of the aforementioned pharmaceutical compositions, the effective dose of the vasoconstrictor is from about 0.1 µg to about 250 µg. In some embodiments of the aforementioned pharmaceutical compositions, the effective dose of the vasoconstrictor is from about 0.1 µg to about 200 µg. In some embodiments of the aforementioned pharmaceutical compositions, the effective dose of the vasoconstrictor is from about 0.1 µg to about 150 µg. In some embodiments of the aforementioned pharmaceutical compositions, the effective dose of the vasoconstrictor is from about 0.5 µg to about 150 µg. In some embodiments of the aforementioned pharmaceutical compositions, the effective dose of the vasoconstrictor is from about 1 µg to about 150 µg. In some embodiments of the aforementioned pharmaceutical compositions, the effective dose of the vasoconstrictor is from about 1 µg to about 125 µg. In some embodiments of the aforementioned pharmaceutical compositions, the effective dose of the vasoconstrictor is from about 1 µg to about 100 µg. In some embodiments of the aforementioned pharmaceutical compositions, the effective dose of the vasoconstrictor is from about 1 µg to about 90 µg. In some embodiments of the aforementioned pharmaceutical compositions, the effective dose of the vasoconstrictor is from about 1 µg to about 75 µg. In some embodiments of the aforementioned pharmaceutical compositions, the effective dose of the vasoconstrictor is from about 1 µg to about 60 µg. In some embodiments of the aforementioned pharmaceutical compositions, the effective dose of the vasoconstrictor is from about 1 µg to about 60 µg. In some embodiments of the aforementioned pharmaceutical compositions, the effective dose of the vasoconstrictor is from about 1 µg to about 50 µg. In some embodiments of the aforementioned pharmaceutical compositions, the effective dose of the vasoconstrictor is from about 1 µg to about 40 µg. In some embodiments of the aforementioned pharmaceutical compositions, the effective dose of the vasoconstrictor is from about 1 µg to about 30 µg. In some embodiments of the aforementioned pharmaceutical compositions, the effective dose of the vasoconstrictor is from 1 µg to about 25 µg. In some embodiments of the aforementioned pharmaceutical compositions, the effective dose of the vasoconstrictor is from about 1 µg to about 20 µg. In some embodiments of the aforementioned pharmaceutical compositions, the effective dose of the vasoconstrictor is from about 1 µg to about 15 µg. In some embodiments of the aforementioned pharmaceutical compositions, the effective dose of the vasoconstrictor is from about 1 µg to about 10 µg. In some 1 µg to about 5 µg. In some embodiments of the aforementioned pharmaceutical compositions, the effective dose of the vasoconstrictor is from about 10 µg to about 150 µg. In some embodiments of the aforementioned pharmaceutical compositions, the effective dose of the vasoconstrictor is from about 10 µg to about 125 µg. In some embodiments of the aforementioned pharmaceutical compositions, the effective dose of the vasoconstrictor is from about 10 µg to about 100 µg. In some embodiments of the aforementioned pharmaceutical compositions, the effective dose of the vasoconstrictor is from about 10 µg to about 75 µg. In some embodiments of the aforementioned pharmaceutical compositions, the effective dose of the vasoconstrictor is from about 10 µg to about 50 µg.

In some embodiments of the aforementioned pharmaceutical compositions, the vasoconstrictor is in a concentration range from about 2 µg/mL to about 10 µg/mL. In some embodiments of the aforementioned pharmaceutical compositions, the vasoconstrictor is in a concentration range from about 2 µg/mL to about 5 µg/mL. In some embodiments of the aforementioned pharmaceutical compositions, the concentration of the vasoconstrictor is about 10 µg/mL. In some embodiments of the aforementioned pharmaceutical compositions, the concentration of the vasoconstrictor is about 9 µg/mL. In some embodiments of the aforementioned pharmaceutical compositions, the concentration of the vasoconstrictor is about 8 µg/mL. In some embodiments of the aforementioned pharmaceutical compositions, the concentration of the vasoconstrictor is about 7 µg/mL. In some embodiments of the aforementioned pharmaceutical compositions, the concentration of the vasoconstrictor is about 6 µg/mL. In some embodiments of the aforementioned pharmaceutical compositions, the concentration of the vasoconstrictor is about 5 µg/mL. In some embodiments of the aforementioned pharmaceutical compositions, the concentration of the vasoconstrictor is about 4 µg/mL. In some embodiments of the aforementioned pharmaceutical compositions, the concentration of the vasoconstrictor is about 3 µg/mL. In some embodiments of the aforementioned pharmaceutical compositions, the concentration of the vasoconstrictor is about 2 µg/mL. In some embodiments of the aforementioned pharmaceutical compositions, the concentration of the vasoconstrictor is about 1 µg/mL.

In some embodiments of the aforementioned pharmaceutical compositions is a pharmaceutical composition for the treatment or prevention of pain, wherein the pain is post-surgical pain, post amputation pain, chronic post-surgical pain, and traumatic injury pain. In some embodiments of the aforementioned pharmaceutical compositions is a pharmaceutical composition for the treatment or prevention of pain, wherein the pain is post-surgical pain. In some embodiments of the aforementioned pharmaceutical compositions is a pharmaceutical composition for the treatment or prevention of pain, wherein the post-surgical pain is pain from a laparotomy, thoracotomy, thoraco-abdominal incision, flank incision, total hip replacement, total knee replacement, ACL reconstruction, rotator cuff repair, bunionectomy, laparoscopy, dental extraction, or open reduction internal fixation of fractures. In some embodiments of the aforementioned pharmaceutical compositions is a pharmaceutical composition for the treatment or prevention of pain, wherein the post-surgical pain is pain from a laparotomy. In some embodiments of the aforementioned pharmaceutical compositions is a pharmaceutical composition for the treatment or prevention of pain, wherein the post-surgical pain is pain from a thoracotomy. In some embodiments of the aforementioned pharmaceutical compositions is a pharmaceutical composition for the treatment or prevention of pain, wherein the post-surgical pain is pain from a thoraco-abdominal incision. In some embodiments of the aforementioned pharmaceutical compositions is a pharmaceutical composition for the treatment or prevention of pain, wherein the post-surgical pain is pain from a flank incision. In some embodiments of the aforementioned pharmaceutical compositions is a pharmaceutical composition for the treatment or prevention of pain, wherein the post-surgical pain is pain from a total hip replacement. In some embodiments of the aforementioned pharmaceutical compositions is a pharmaceutical composition for the treatment or prevention of pain, wherein the post-surgical pain is pain from a total knee replacement. In some embodiments of the aforementioned pharmaceutical compositions is a pharmaceutical composition for the treatment or prevention of pain, wherein the post-surgical pain is pain from an ACL reconstruction. In some embodiments of the aforementioned pharmaceutical compositions is a pharmaceutical composition for the treatment or prevention of pain, wherein the post-surgical pain is pain from a rotator cuff repair. In some embodiments of the aforementioned pharmaceutical compositions is a pharmaceutical composition for the treatment or prevention of pain, wherein the post-surgical pain is pain from a bunionectomy. In some embodiments of the aforementioned pharmaceutical compositions is a pharmaceutical composition for the treatment or prevention of pain, wherein the post-surgical pain is pain from a laparoscopy. In some embodiments of the aforementioned pharmaceutical compositions is a pharmaceutical composition for the treatment or prevention of pain, wherein the post-surgical pain is pain from a dental extraction. In some embodiments of the aforementioned pharmaceutical compositions is a pharmaceutical composition for the treatment or prevention of pain, wherein the post-surgical pain is pain from an open reduction internal fixation of fractures. In some embodiments of the aforementioned pharmaceutical compositions is a pharmaceutical composition for the treatment or prevention of pain, wherein the pain is post amputation pain. In some embodiments of the aforementioned pharmaceutical compositions is a pharmaceutical composition for the treatment or prevention of pain, wherein the pain is chronic post-surgical pain. In some embodiments of the aforementioned pharmaceutical compositions is a pharmaceutical composition for the treatment or prevention of pain, wherein the pain is chronic post-surgical pain after mastectomy or lumpectomy referred to as "post mastectomy syndrome". In some embodiments of the aforementioned pharmaceutical compositions is a pharmaceutical composition for the treatment or prevention of pain, wherein the pain is chronic post-surgical pain after thoracotomy. In some embodiments of the aforementioned pharmaceutical compositions is a pharmaceutical composition for the treatment or prevention of pain, wherein the pain is chronic post-surgical pain after amputation referred to as "stump pain". In some embodiments of the aforementioned pharmaceutical compositions is a pharmaceutical composition for the treatment or prevention of pain, wherein the pain is traumatic injury pain. In some embodiments of the aforementioned pharmaceutical compositions is a pharmaceutical composition for the treatment or prevention of pain, wherein the pain is traumatic injury pain from a long bone, short bone, flat bone, or irregular bone fracture. In some embodiments of the aforementioned pharmaceutical compositions is a pharmaceutical composition for the treatment or prevention of pain, wherein the pain is traumatic injury pain from a long bone fracture. In some embodiments of the aforementioned pharmaceutical compositions is a pharmaceutical composition for the treatment or prevention of pain, wherein the pain is traumatic injury pain from a short bone fracture. In some embodiments of the aforementioned pharmaceutical compositions is a pharmaceutical composition for the treatment or prevention of pain, wherein the pain is traumatic injury pain from a flat bone fracture. In some embodiments of the aforementioned pharmaceutical compositions is a pharmaceutical composition for the treatment or prevention of pain, wherein the pain is traumatic injury pain from an irregular bone fracture. In some embodiments of the aforementioned pharmaceutical compositions is a pharmaceutical composition for the treatment or prevention of pain, wherein the traumatic injury pain is pain from a hip or rib fracture. In some embodiments of the aforementioned pharmaceutical compositions is a pharmaceutical composition for the treatment or prevention of pain, wherein the traumatic injury pain is pain from a hip fracture. In some embodiments of the aforementioned pharmaceutical compositions is a pharmaceutical composition for the treatment or prevention of pain, wherein the traumatic injury pain is pain from a rib fracture.

In some embodiments of the aforementioned pharmaceutical compositions is a pharmaceutical composition for the treatment or prevention of pain, wherein the pain is chronic pain. In some embodiments of the aforementioned methods is a method of treating or preventing pain in a subject in need thereof, wherein the pain is chronic pain associated with osteoarthritis. In some embodiments of the aforementioned pharmaceutical compositions is a pharmaceutical composition for the treatment or prevention of pain, wherein the pain is chronic pain associated with osteoarthritis of the knee. In some embodiments of the aforementioned pharmaceutical compositions is a pharmaceutical composition for the treatment or prevention of pain, wherein the pain is chronic musculoskeletal pain. In some embodiments of the aforementioned pharmaceutical compositions is a pharmaceutical composition for the treatment or prevention of pain, wherein the pain is musculoskeletal pain of the lower back.

In some embodiments of the aforementioned pharmaceutical compositions, the effective dose is in a dosing volume from about 10 mL to about 120 mL. In some embodiments of the aforementioned pharmaceutical compositions, the effective dose is in a dosing volume from about 10 mL to about 110 mL. In some embodiments of the aforementioned pharmaceutical compositions, the effective dose is in a dosing volume from about 10 mL to about 100 mL. In some embodiments of the aforementioned pharmaceutical compositions, the effective dose is in a dosing volume from about 10 mL to about 90 mL. In some embodiments of the aforementioned pharmaceutical compositions, the effective dose is in a dosing volume from about 10 mL to about 80 mL. In some embodiments of the aforementioned pharmaceutical compositions, the effective dose is in a dosing volume from about 10 mL to about 70 mL. In some embodiments of the aforementioned pharmaceutical compositions, the effective dose is in a dosing volume from about 10 mL to about 60 mL. In some embodiments of the aforementioned pharmaceutical compositions, the effective dose is in a dosing volume from about 10 mL to about 50 mL. In some embodiments of the aforementioned pharmaceutical compositions, the effective dose is in a dosing volume from about 10 mL to about 40 mL. In some embodiments of the aforementioned pharmaceutical compositions, the effective dose is in a dosing volume from about 10 mL to about 30 mL. In some embodiments of the aforementioned pharmaceutical compositions, the effective dose is in a dosing volume from about 10 mL to about 25 mL. In some embodiments of the aforementioned pharmaceutical compositions, the effective dose is in a dosing volume from about 10 mL to about 30 mL. In some embodiments of the aforementioned pharmaceutical compositions, the effective dose is in a dosing volume from about 30 mL to about 120 mL. In some embodiments of the aforementioned pharmaceutical compositions, the effective dose is in a dosing volume from about 30 mL to about 100 mL. In some embodiments of the aforementioned pharmaceutical compositions, the effective dose is in a dosing volume from about 30 mL to about 90 mL. In some embodiments of the aforementioned pharmaceutical compositions, the effective dose is in a dosing volume from about 30 mL to about 80 mL. In some embodiments of the aforementioned pharmaceutical compositions, the effective dose is in a dosing volume less than about 10 mL. In some embodiments of the aforementioned pharmaceutical compositions, the effective dose is in a dosing volume of about 10 mL. In some embodiments of the aforementioned pharmaceutical compositions, the effective dose is in a dosing volume of about 8 mL. In some embodiments of the aforementioned pharmaceutical compositions, the effective dose is in a dosing volume of about 6 mL. In some embodiments of the aforementioned pharmaceutical compositions, the effective dose is in a dosing volume of about 5 mL. In some embodiments of the aforementioned pharmaceutical compositions, the effective dose is in a dosing volume of about 4 mL. In some embodiments of the aforementioned pharmaceutical compositions, the effective dose is in a dosing volume of about 3 mL. In some embodiments of the aforementioned pharmaceutical compositions, the effective dose is in a dosing volume of about 2 mL. In some embodiments of the aforementioned pharmaceutical compositions, the effective dose is in a dosing volume of about 1 mL.

In some embodiments of the aforementioned methods, the subject is awake. In some embodiments of the aforementioned methods, the subject is sedated.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999), herein incorporated by reference for such disclosure.

A pharmaceutical composition, as used herein, refers to a mixture of Compound 1 with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a subject having a disease, disorder, or condition to be treated. In some embodiments, the subject is a human. A therapeutically effective amount can vary widely depending on the severity of the disease, the age and relative health of the subject, the potency of the compound used and other factors. Compound 1 can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein can be formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

One may administer the compounds and/or compositions in a local rather than systemic manner, for example, via injection of the compound directly into an organ or tissue, often in a depot preparation. Such formulations may be administered by implantation (for example subcutaneously or intramuscularly) or by intramuscular injection. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, as an active ingredient in free-acid or free-base form, or in a pharmaceutically acceptable salt form. In addition, the methods and pharmaceutical compositions described herein include the use of crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, saline, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or nonaqueous solutions, preferably with physiologically compatible buffers or excipients. Such excipients are generally recognized in the field.

In some embodiments described herein, Compound 1 is formulated in an aqueous solution. In some embodiments described herein, Compound 1 is formulated in an acidic aqueous solution. In some embodiments described herein, Compound 1 is a powder that is reconstituted at the time of use as an aqueous solution. In some embodiments described herein is a pharmaceutical composition for the treatment or prevention of pain, wherein the pharmaceutical composition comprises an effective dose of Compound 1, and a pharmaceutically acceptable carrier, wherein the effective dose of Compound 1 is from about 0.01 mg to about 25 mg and the carrier is sterile water. In some embodiments described herein is a pharmaceutical composition for the treatment or prevention of pain, wherein the pharmaceutical composition comprises an effective dose of Compound 1, and a pharmaceutically acceptable carrier, wherein the effective dose of Compound 1 is from about 0.01 mg to about 25 mg and the carrier is sterile saline.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Pharmaceutical preparations for oral use can be obtained by mixing one or more solid excipient with Compound 1, optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

The term "rapid release" or "delayed release" as used herein refers to the delivery so that the release can be accomplished at some generally predictable rate. In some embodiments the method for delay of release is either the tuning of the intramolecular cyclization-release reaction or via the addition of buffers to modify the initiation of the intramolecular cyclization-release reaction.

In some embodiments, pharmaceutical formulations are provided that include particles of Compound 1, and at least one dispersing agent or suspending agent for oral administration to a subject. The formulations may be a powder and/or granules for suspension, and upon admixture with water, a substantially uniform suspension is obtained.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960,563.

There is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Potential excipients for intranasal formulations include, for example, U.S. Pat. Nos. 4,476,116, 5,116,817 and 6,391,452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable non-toxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Compound 1 is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

The particular delivery system used can depend on a number of factors, including, for example, the intended target and the route of administration, e.g., local or systemic. Targets for delivery can be specific cells which are causing or contributing to a disease or disorder. For example, a target cell can be resident or infiltrating cells in the nervous system contributing to a neurological, neurodegenerative or demyelinating disease or disorder. Administration of an agent can be directed to one or more cell types or subsets of a cell type by methods recognized in the field. For example, an agent can be coupled to an antibody, ligand to a cell surface receptor or a toxin, or can be contained in a particle that is selectively internalized into cells, e.g., liposomes or a virus in which the viral receptor binds specifically to a certain cell type, or a viral particle lacking the viral nucleic acid, or can be administered locally.

Methods of Dosing and Treatment Regimens

Compound 1 described herein can be used in the preparation of medicaments for the modulation of TRPV1, or for the treatment of diseases or conditions that would benefit, at least in part, from modulation of TRPV1. In addition, a method for treating any of the diseases or conditions described herein in a subject in need of such treatment, involves administration of a pharmaceutical composition containing Compound 1 described herein.

The compositions containing Compound 1 described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing Compound 1 described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder, or condition, previous therapy, the patient's health status and response to the drugs, and the judgment of the treating physician.

Upon the doctor's discretion, the administration of Compound 1 may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder, or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.001 mg per day to about 5000 mg per day, in some embodiments, about 1 mg per day to about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Combination Treatments

In some embodiments, described herein are combination treatments comprising Compound 1, and at least one of a local anesthetic and vasoconstrictor. In general, the compositions described herein and, in embodiments where combinational therapy is employed, the agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one of Compound 1, and at least one of a local anesthetic and vasoconstrictor described herein in combination with another therapeutic agent. By way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder, or condition being treated, the overall benefit experienced by the patient may simply be additive of the therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents described herein may be administered in any order or even simultaneously. If simultaneously, the multiple therapeutic agents may be provided in a single, unified form, or in multiple forms (by way of example only, either as a single injection or as two separate injections). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder, or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. In some embodiments, the kit is a two chamber container that holds the local anesthetic (liquid) and compound 1 (solid) to facilitate sterile reconstitution.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Example 1: Synthesis of (E)-2-methoxy-4-((8-methylnon-6-enamido)methyl)phenyl 2-((methylamino)methyl)piperidine-1-carboxylate hydrochloride (Compound 1)

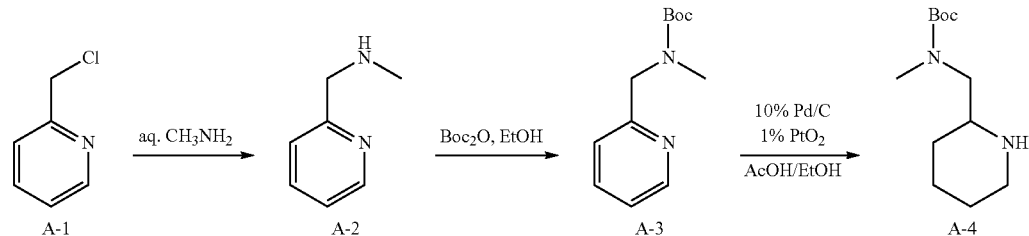

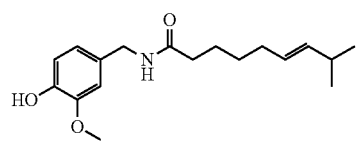

Capsaicin

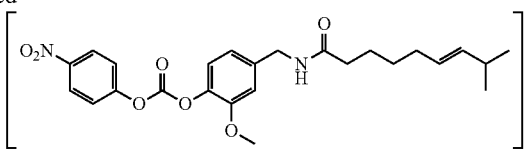

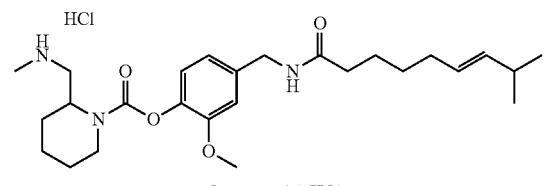 [SMILES: Cl ; CNCC1CCCCN1C(=O)Oc1ccc(CNC(=O)CCCC/C=C/C(C)C)cc1OC]

Compound 1-HCl

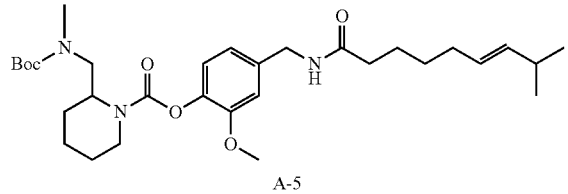

A-5

Preparation of Compound A-2

2-(Chloromethyl)pyridine (1.0 eq) was dissolved in water and added dropwise to a solution of 40% aq. Methylamine (20.0 eq) at <5° C. over 2.5 h, maintaining the reaction temperature at 5° C. After the addition was complete, the reaction was warmed to room temperature over 30 min, then concentrated to red oil/solid. This was dissolved in water and cooled to 10° C. Then cold 50% aq. NaOH (4° C., 2.5 eq) was added over 20 min, and the suspension warmed to 40° C. The biphasic suspension was then cooled to room temperature and the salt was filtered. The filtrate was removed and the layers were separated. The filter cake was rinsed with iPrOAc and the iPrOAc filtrate was used to extract the aqueous portion of the initial filtrate. The iPrOAc layer was concentrated with a rotary evaporator and the resulting oil was combined with the organic portion of the initial filtrate. The resulting red oil was concentrated under high vacuum overnight. The flask was then fitted with a distillation head and the product distilled with a B.P. of 67° C. @ 5 Torr to afford compound A-2.

Preparation of Compound A-3

Compound A-2 (1.0 eq) was dissolved in EtOH and cooled to 10° C. Then a solution of Boc$_2$O (1.0 eq) in EtOH was added drop-wise over 60 min, maintaining the reaction temperature <20° C. Gas was evolved during the addition. After the addition, the solution was warmed to room temperature and stirred for 60 minutes, until gas evolution ceased. Then HPLC indicated complete conversion to A-3. The crude product was used in the following reaction without further manipulation.

Preparation of Compound A-4

To the crude product mixture from the synthesis of A-3 (see above) was added acetic acid (10 eq.), followed by catalyst, 10 wt % (wet) Pd/C (10 wt %/C) and 1 wt % PtO$_2$ (10 wt %/C). The suspension was placed under a H$_2$ atmosphere and shaken under 55 PSI H$_2$ with a Parr shaker for 9 days. The suspension was filtered through celite under argon and concentrated with a rotary evaporator. The mixture was further concentrated with high vacuum overnight to afford A-4 as the acetate salt.

Preparation of Compound A-5

To a reaction flask charged with capsaicin (1 eq) and ethyl acetate, the solution was cooled to 0-10° C. and DIPEA (3 eq) was added followed by the addition of nitrophenylchloroformate (1.0 eq) as a solution in ethyl acetate at 0-10° C. The resulting mixture was stirred at 0-10° C. for 15 min. Next, HOBt (0.1 eq) was added, followed by A-4 free base (1.2 eq) at 0-10° C. The resulting mixture was stirred overnight after warming to room temperature. The reaction mixture was worked up by successive extractions with 1M aq. NaOH (3×), 1M aq. HCl, water and finally brine solution. The resulting organic layer was removed, dried over sodium sulfate and filtered to afford A-5 as the ethyl acetate solution. The crude product was used in the following reaction without further manipulation.

Preparation of Compound 1

To the crude product mixture from the synthesis of A-5 (see above), the mixture was cooled to 0-10° C. with stirring and sparged with HCl (g) for approximately 30 seconds. The resulting mixture was stirred at 0-10° C. for approximately 2 h. The resulting mixture was concentrated and Compound 1 was purified via crystallization in EtOAc.

Example 2: Pharmacokinetic Data—Plasma Timecourse Following SC Administration to Rat This Example compares the pharmacokinetics of capsaicin from either capsaicin or from Compound 1 (with or without co-administered bupivacaine or bupivacaine with epinephrine) administered subcutaneously (SC) to rats. Additionally, this example compares the pharmacokinetics of cyclic urea metabolite (Compound 2) from Compound 1 (with or without co-administered bupivacaine or bupivacaine with epinephrine).

SC dosing: Four groups of six male Sprague-Dawley rats (vendor was Charles River Laboratories) each were to receive a single subcutaneous dose (4 mL/kg) of one of the following test articles:

Group 1) 1.00 mg/kg capsaicin in 25% PEG300/sterile water for injection (♦);
Group 2) 1.62 mg/kg Compound 1.HCl in sterile water for injection (□);
Group 3) 1.62 mg/kg Compound 1.HCl in 0.25% bupivacaine hydrochloride for injection (Δ);
Group 4) 1.62 mg/kg Compound 1.HCl in 0.25% bupivacaine hydrochloride plus epinephrine, (1:200,000 for injection) (*).

The dose of capsaicin and Compound 1 were selected to provide approximately equimolar amounts.

The injection volume was 4 mL/kg. (Note: The actual dose of capsaicin for Group 1 was 0.74 mg/kg, or 74% of the intended dose of 1 mg/kg. Dose data represents dose correction of Group 1 to equimolar dosages with Compound 1 from groups 2, 3, 4). The actual doses of Compound 1 HCl and bupivacaine for Groups 2, 3, and 4 were within 10% of the intended doses.

Blood samples (0.3 mL) were collected from the jugular vein into tubes containing $K_2$EDTA as anticoagulant and 0.3 ml of 2% formic acid (resulting in a final concentration of 1% formic acid) as a quenching agent to stop the cyclization of Compound 1, which releases capsaicin and cyclic urea Compound 2. The samples were collected from each rat at 2, 10, and 30 minutes, and 1, 2, 4, 8, and 24 hours post-dose.

Each blood sample was mixed by inversion and placed on dry ice. They were not processed for plasma. The blood samples were kept frozen at −70° C. until further processing and analysis was performed. All blood samples were collected as scheduled.

The concentrations of the two main analytes in rat blood mixed 1:1 (v/v) with 2% formic acid were determined simultaneously using a qualified LC-MS/MS assay. The results for both analytes were reported in ng/mL. The calibration range was 1 to 1,000 ng/mL for Compound 1 and capsaicin in the mixed matrix. The calibration range was 5 to 1,000 ng/mL for Compound 2.

Figure 2:
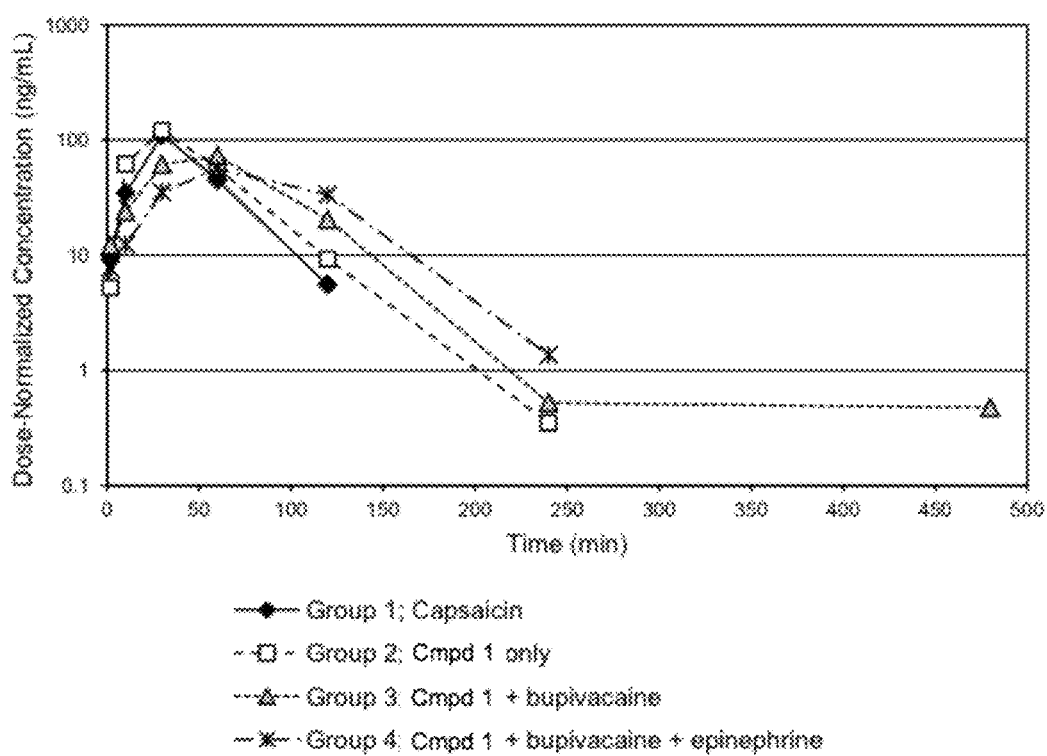
FIG. 2 shows the same data as in FIG. 1 (measurable whole blood concentrations of capsaicin vs. time following subcutaneous (SC) dosing in rats) as a semi-log plot.

Table 1, FIG. 1, and FIG. 2 provide dose-corrected capsaicin exposure results for rats administered as described above. Results in Table 1 are reported, for each group of rats, as (a) maximum plasma concentration (Cmax) of capsaicin (average±standard deviation), (b) time after administration of test article for capsaicin to reach maximum concentration (Tmax) (average±standard deviation), and (c) area under the curve (AUC) from 0 to 24 h for capsaicin (average±standard deviation).

TABLE 1

PK parameters for Capsaicin from Groups 1-4

| Parameter | Group | Mean ± SD | % CV | Median | Range | n |
|---|---|---|---|---|---|---|
| $C_{max}$ | 1 | 110 ± 41 | 36.8 | 105 | 712-180 | 6 |
| (ng/mL)/ | 2 | 121 ± 33 | 27.2 | 124 | 66.4-166 | 6 |
| (mg/kg) | 3 | 75.7 ± 19.6 | 25.9 | 80.1 | 44.8-96.3 | 6 |
|  | 4 | 60.8 ± 9.5 | 15.6 | 57.9 | 51.4-74.7 | 6 |
| $T_{max}$ | 1 | 30.0 ± 0 | 0 | 30 | 30-30 | 6 |
| (min) | 2 | 26.7 ± 8.2 | 30.6 | 30 | 10-30 | 6 |
|  | 3 | 50.0 ± 15.5 | 31.0 | 60 | 30-60 | 6 |
|  | 4 | 65.0 ± 29.5 | 45.4 | 60 | 30-120 | 6 |
| $AUC_{0-24}$ | 1 | 5,799 ± 1,759 | 30.3 | 5,193 | 4,157-9,136 | 6 |
| (ng · min/mL)/ | 2 | 7,380 ± 1,308 | 17.7 | 7,039 | 6,128-9,576 | 6 |
| (mg/kg) | 3 | 7,417 ± 2,136 | 28.8 | 8,076 | 4,150-9,896 | 6 |
|  | 4 | 6,878 ± 693 | 10.1 | 6,578 | 6,172-8,028 | 6 |

The results in Table 1, FIG. 1, and FIG. 2 demonstrate that the use of epinephrine, in combination with Compound 1 and bupivacaine shows: 1) reduced blood levels of capsaicin prior to the Tmax; 2) reduced capsaicin levels at Cmax; 3) delayed Tmax for capsaicin blood levels; and 4) increased blood levels of capsaicin post Tmax, when compared to either dosing of Compound 1 alone or in combination with bupivacaine alone.

Figure 3:
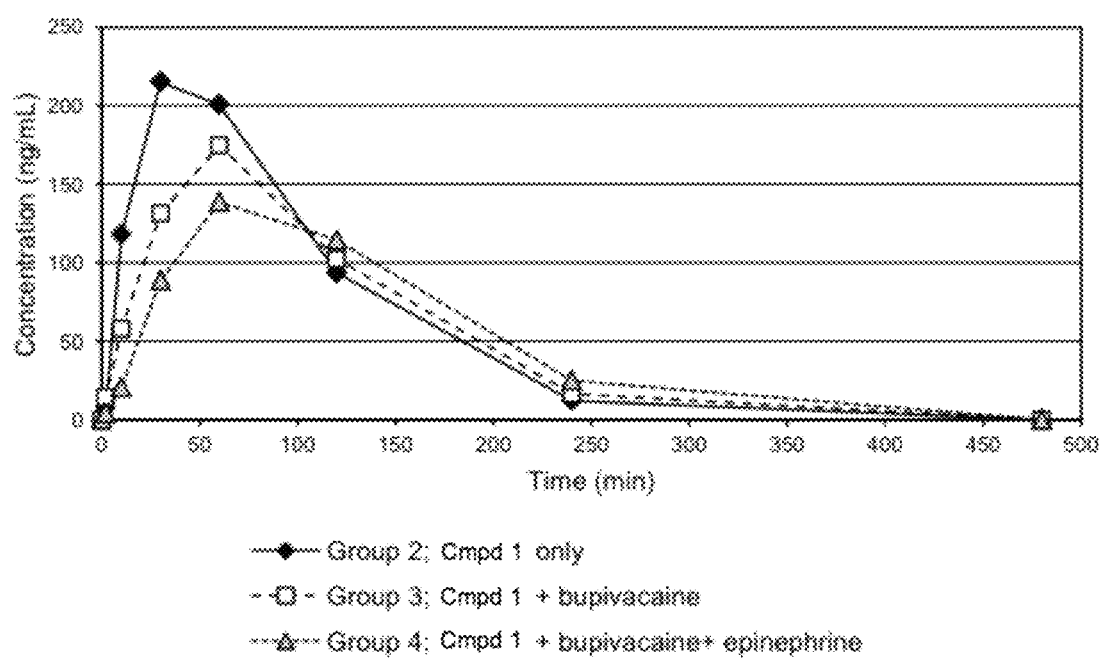
FIG. 3 shows the measurable whole blood concentrations of Compound 2 vs. time following subcutaneous (SC) dosing in rats (linear plot). Group 2 (♦) represents the blood concentration of Compound 2 following SC dosing of Compound 1 HCl (1.62 mg/kg) in sterile water. Group 3 (□) represents the blood concentration of Compound 2 following SC dosing of Compound 1 HCl (at 1.62 mg/kg) in 0.25% bupivacaine hydrochloride solution. Group 4 (Δ) represents the blood concentration of Compound 2 following SC dosing of Compound 1 HCl (at 1.62 mg/kg) in 0.25% bupivacaine hydrochloride solution plus epinephrine (1:200,000) solution).
Figure 4:
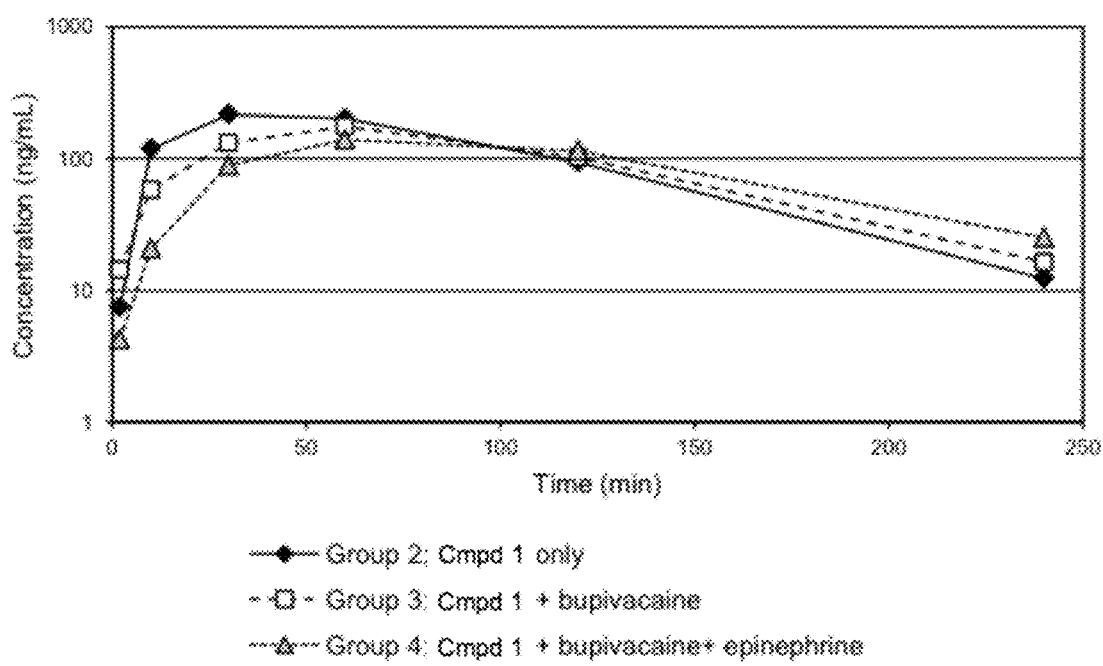
FIG. 4 shows the same data as in FIG. 3 (measurable whole blood concentrations of Compound 2 vs. time following subcutaneous (SC) dosing in rats) as a semi-log plot.

Table 2, FIG. 3, and FIG. 4 provide Compound 2 exposure results for rats administered as described above. Results in Table 2 are reported, for each group of rats, as (a) maximum plasma concentration (Cmax) of Compound 2 (average±standard deviation), (b) time after administration of test article for Compound 2 to reach maximum concentration (Tmax) (average±standard deviation), and (c) area under the curve (AUC) from 0 to 24 h for Compound 2 (average±standard deviation).

TABLE 2

PK parameters for Compound 2 from Groups 2-4

| Paramter | Group | Mean ± SD | % CV | Median | Range | n |
|---|---|---|---|---|---|---|
| $C_{max}$ | 2 | 226 ± 37 | 16.3 | 226 | 166-264 | 6 |
| (ng/mL) | 2 | 175 ± 48 | 27.3 | 196 | 88.2-216 | 6 |
|  | 3 | 142 ± 16 | 11.2 | 149 | 113-155 | 6 |
| $T_{max}$ | 2 | 36.7 ± 19.7 | 53.6 | 30 | 10-60 | 6 |
| (min) | 3 | 60.0 ± 0 | 0.0 | 60 | 60-60 | 6 |
|  | 4 | 65.0 ± 29.5 | 45.4 | 60 | 30-120 | 6 |
| $AUC_{0-24}$ | 2 | 26,713 ± 2,452 | 9.2 | 27,008 | 23,696-29,994 | 6 |
| (ng · | 3 | 24,180 ± 7,095 | 29.3 | 25,930 | 10,285-30,025 | 6 |
| min/mL) | 4 | 23,561 ± 1,605 | 6.8 | 22,822 | 22,267-26,255 | 6 |

The results in Table 2, FIG. 3, and FIG. 4 demonstrate that the use of epinephrine, in combination with Compound 1 and bupivacaine shows: 1) reduced blood levels of Compound 2 prior to the Tmax; 2) reduced Compound 2 levels at Cmax; 3) delayed Tmax for Compound 2 blood levels; and 4) increased blood levels of Compound 2 post Tmax, when compared to either dosing of Compound 1 alone or in combination with bupivacaine alone.

Example 3: Pharmacodynamic Data—Efficacy of Compound 1 in the Brennan Model of Post-Incisional Pain in Rat This Example compares the pharmacodynamics of capsaicin from either capsaicin or from Compound 1 (with or without co-administered bupivacaine or bupivacaine with epinephrine) administered via intraplantar infiltration to rats.

Intraplantar infiltration dosing: Four groups of six male CD rats (vendor was Charles River Laboratories) each were to receive a single subcutaneous dose of one of the following test articles:

Group 1. 0.5% Bupivacaine solution with epinephrine (1:200,000), 0.875 mg
Group 2. Capsaicin, 100 µg in 25% PEG300/saline (v/v)
Group 3. Capsaicin, 100 µg in 0.5% bupivacaine solution (in 25% PEG300, based on volume)
Group 4. Compound 1, 81 µg in 0.9% saline
Group 5. Compound 1, 81 µg in 0.5% bupivacaine solution
Group 6. Compound 1, 162 µg in 0.9% saline
Group 7. Compound 1, 162 µg in 0.5% bupivacaine solution
Group 8. Compound 1, 162 µg in 0.5% bupivacaine solution plus epinephrine (1:200,000)
Group 9. Compound 1, 243 µg in 0.5% bupivacaine solution plus epinephrine (1:200,000)
Group 10. Vehicle control (0.9% Saline).

The injection volume was 175 µL per rat. Vehicle and test articles will be administered by wound intraplantar infiltration (150 µL) immediately prior to incision, and injection into flexor muscle prior to closure (25 µL).

Surgery: Animals were anesthetized with 1.8 to 4% isofluorane (delivered via a nose cone) and each received an intramuscular injection of penicillin (30,000 IU) in the triceps muscle after preparation of the foot with betadine and alcohol (SOPs VET-1 and VET-8). Study drug (150 µL) was infiltrated (by intraplantar injection) immediately prior to incision. A 1 cm long incision of skin, fascia and muscle will be made in the plantar aspect (heel, midfoot or distal pad area) of the right hind paw starting 0.5 cm from the proximal edge of the heel and extending towards the toes. The flexor muscle was elevated and incised longitudinally via blunt dissection with the muscle origin and insertion remaining intact. After hemostasis with gentle pressure, study drug (25 µL) was injected into the flexor muscle prior to closure, and the incision was closed with one or two sutures (5-0 silk/nylon ophthalmic suture on a taper TF needle or equivalent).

The wound site was covered with a mixture of polymixin B, neomycin, and bacitracin ointment. After surgery, rats were allowed to recover in their cages until behavioral testing.

Guarding Behaviors: The rats were placed in Plexiglas® squares on a stainless steel wire mesh floor thirty minutes before guarding scores are to be measured for acclimation. Guarding scores were measured over 1 hour time periods for the incised paw. The animals were observed closely during a 60 second period every 5 minutes for 1 hour and scored as follows. Depending on the position in which the paw is found during the majority of the 20-30 second period, the scoring were as follows:

0—Full weight bearing of the paw present if the wound is blanched or distorted by the mesh.
1—If the area of the wound touches the mesh gently without any blanching or distorting.
2—If the paw is completely off the mesh without any touch.

Figure 5:
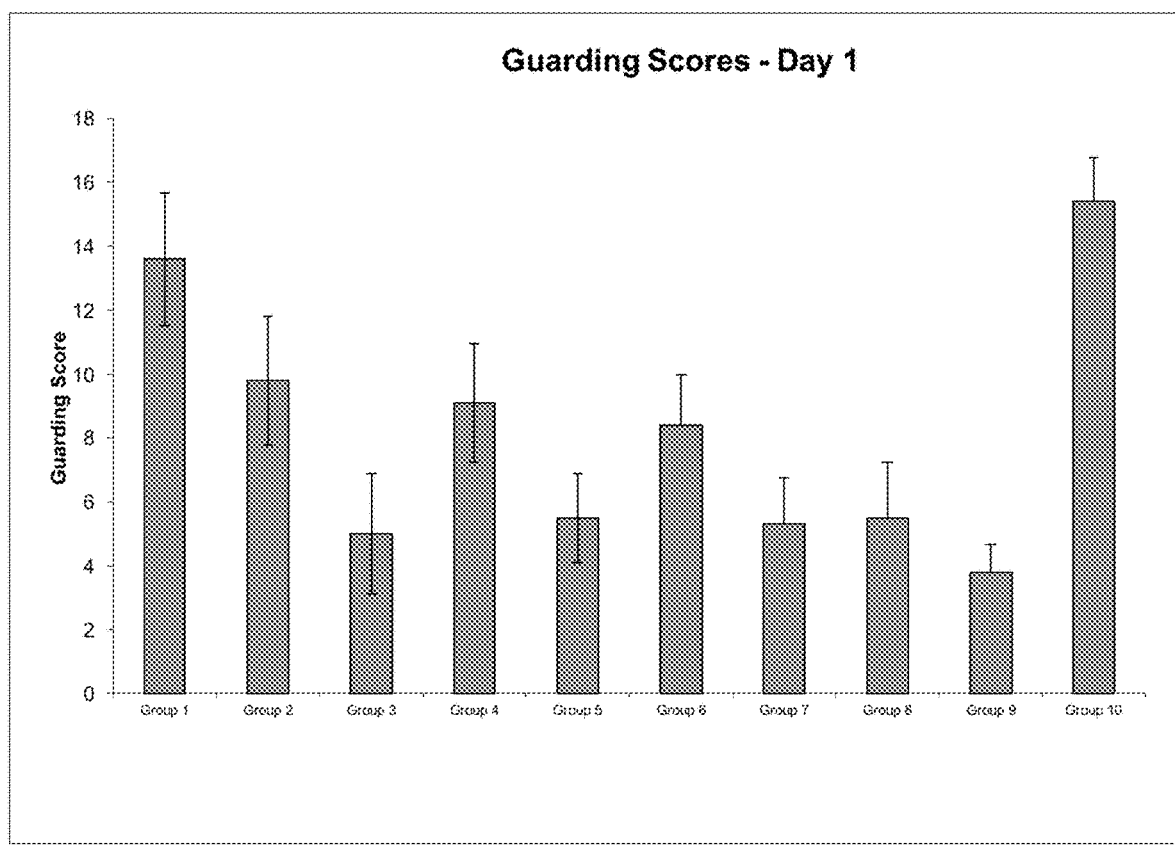
FIG. 5 shows guarding scores measured for the incised paw of test compounds in the Brennan Model of Post-Incisional Pain in rat at Day 1 for the following groups.

The sum of the 12 scores obtained during the 1 hour test session (total scores: 0-24) were obtained for each rat. Guarding scores were taken over a 1 hour period as follows: on the day prior to surgery, beginning four hours (±30 minutes) post completion of surgery (Day 1); and once daily on Days 2, 3, 4 and 7. Data for Day 1 is shown in FIG. 5. The test data demonstrate that the two-way combination of Compound 1 and bupivacaine and the three-way combination of Compound 1, bupivacaine, and epinephrine dosed according to the invention are capable of providing effective analgesia via post administration-activated, prodrug delivery of a TRPV1 agonist (capsaicin) and a local anesthetic (bupivacaine), with enhanced localized delivery via the use of a vasoconstrictor (epinephrine), especially when compared to capsaicin or Compound 1 alone.

Example 4: Pharmacodynamic Data—Efficacy of Compound 1 in the Brennan Model of Post-Incisional Pain in Rat This Example compares the pharmacodynamics of capsaicin from either capsaicin or from Compound 1 (with or without co-administered bupivacaine or ropivacaine) administered via intraplantar infiltration to rats.

Intraplantar infiltration dosing: Five groups of eight male Sprague Dawley rats (vendor was Charles River Laboratories) each were to receive a single subcutaneous dose of one of the following test articles:

Group 1. Compound 1, 162 µg in 0.25% bupivacaine solution (175 µL)
Group 2. Compound 1, 162 µg in 0.25% ropivacaine solution (175 µL)
Group 3. Compound 1, 162 µg in 0.125% ropivacaine solution (175 µL)
Group 4. 0.25% Ropivacaine solution (175 µL)
Group 5. Vehicle control (0.9% Saline; 175 µL)

The injection volume was 175 µL per rat. Vehicle and test articles will be administered by wound intraplantar infiltration (150 µL) immediately prior to incision, and injection into flexor muscle prior to closure (25 µL).

Surgery: Animals were anesthetized with 1.8 to 4% isofluorane (delivered via a nose cone). Study drug (15 µL) was infiltrated (by intraplantar injection) immediately prior to incision. A 1 cm long incision of skin, fascia and muscle will be made in the plantar aspect (heel, midfoot or distal pad area) of the right hind paw starting 0.5 cm from the proximal edge of the heel and extending towards the toes. The flexor muscle was elevated and incised longitudinally via blunt dissection with the muscle origin and insertion remaining intact. After hemostasis with gentle pressure, study drug (25 µL) was injected into the flexor muscle prior to closure, and the incision was closed with one or two sutures (5-0 silk/nylon ophthalmic suture on a taper TF needle or equivalent). The wound site was covered with a mixture of polymixin B, neomycin, and bacitracin ointment. After surgery, rats were allowed to recover in their cages until behavioral testing.

Guarding Behaviors: The rats were placed in Plexiglas® squares on a stainless steel wire mesh floor thirty minutes before guarding scores are to be measured for acclimation. Guarding scores were measured over 1 hour time periods for the incised paw. The animals were observed closely during a 60 second period every 5 minutes for 1 hour and scored as follows. Depending on the position in which the paw is found during the majority of the 20-30 second period, the scoring were as follows:

0—Full weight bearing of the paw present if the wound is blanched or distorted by the mesh.
1—If the area of the wound touches the mesh gently without any blanching or distorting.
2—If the paw is completely off the mesh without any touch.

The sum of the 12 scores obtained during the 1 hour test session (total scores: 0-24) were obtained for each rat. Guarding scores were taken over a 1 hour period as follows: on the day prior to surgery, beginning four hours (±30 minutes) post completion of surgery (Day 1); and once daily on Days 2, 3, 4 and 7. Data for Day 1 is shown in Table 3. Statistically significant ($p<0.05$) decreases in mean guarding scores were observed on Day 1 in the groups of animals administered 162 µg Compound 1 in 0.25% bupivacaine (Group 1), 162 µg Compound 1 in 0.25% ropivacaine (Group 2), 162 µg Compound 1 in 0.125% bupivacaine (Group 3), when compared to the 0.9% saline group (Group 5). There were no significant changes in mean guarding scores on Day 1 in the group of animals administered 0.25% ropivacaine (Group 4) compared to the saline group (Group 5).

TABLE 3

| Group: | Group | Dose of Compound 1 | Guarding Score (Mean ± SEM) Predose | Day 1 |
|---|---|---|---|---|
| 1 | Cmpd 1 in 0.25% Bupivacaine | 162 µg | 1.0 ± 0.38 | 4.3 ± 0.90 |
| 2 | Cmpd 1 in 0.25% Ropivacaine | 162 µg | 0.9 ± 0.30 | 5.5 ± 1.02 |
| 3 | Cmpd 1 in 0.125% Ropivacaine | 162 µg | 1.3 ± 0.31 | 6.6 ± 0.60 |
| 4 | 0.25% Ropivacaine | 0.0 | 1.1 ± 0.30 | 13.5 ± 1.17 |
| 5 | Vehicle (0.9% Saline) | 0.0 | 1.4 ± 0.26 | 15.0 ± 0.78 |

Data presented as mean ± standard error of the mean.

Example 5: Efficacy of Compound 1 in Comparison to Standard of Care for the Treatment of Post Operative Dental Implant Pain This study is researching managing postsurgical pain by injecting both short-acting local anesthetics and Compound 1 at the time of surgery and reviewing if it could reduce or eliminate the need for postsurgical opioids and improve clinical outcomes following dental implant surgery procedure. This approach is being compared to the current standard of care.

Patients: Eligible subjects will be men and women 18 years of age and older.

Criteria:

Inclusion Criteria:
  Age 18 years or older;
  Ability to speak, read, and write in English;
  Ability to communicate via telephone;
  Scheduled to undergo dental implant surgery procedure at a study center within the next 30 days for both maxillary and mandibular repair with at least 4 upper and 4 lower teeth to be extracted;

Willing to provide informed consent, participate in study, and comply with study protocol.

Exclusion Criteria:
Daily opioid consumption for more than 30 days prior to surgery;
Any opioid consumption within 3 days prior to surgery.
Prior treatment for alcohol, recreational drug, or opioid abuse.
Hypersensitivity or allergy to local anesthetics, non-steroidal anti-inflammatory drugs, or opioids;
Breastfeeding, pregnant, or contemplating pregnancy prior to surgery.

Study Design:
Allocation: Randomized
Endpoint Classification: Safety/Efficacy Study
Intervention Model: Parallel Assignment
Masking: Double Blind (Subject, Investigator)
Primary Purpose: Treatment Primary Outcome Measures:
Postsurgical Pain Severity [Time Frame: 7 days] [Designated as safety issue: No].

Secondary Outcome Measures:
Food ingesting tolerance [Time Frame: 7 days] [Designated as safety issue: No] Ability to ingest different foods
Analgesic medication use [Time Frame: 7 days] [Designated as safety issue: No]
Patient Satisfaction [Time Frame: 7 days] [Designated as safety issue: No] Patient satisfaction with pain control
Incidence of ORAEs and other adverse events (AEs) [Time Frame: 7 days] [Designated as safety issue: Yes]

| Arms | Assigned Interventions |
| --- | --- |
| Experimental: Compound 1 and Local Anesthetics<br>In the experimental group, patients will receive Compound 1 and local anesthetics, and will be prescribed opioid and non-opioid analgesics (for use only if in pain). | Procedure: Compound 1 and Local Anesthetics<br>Patients will receive Compound 1 and local anesthetics, as well as opioid and non-opioid analgesics prescription, (only use if needed, for post-surgical pain) |
| Active Comparator: Oral Opioid and Local Anesthetics<br>In the control group, patients will receive local anesthetics at the time of surgery and oral opioid or non-opioid analgesics (for use only if in pain). | Procedure: Oral Opioid and Local Anesthetics<br>Patients will receive local anesthetics, as well as oral opioid or non-opioid analgesics, (only use if needed, for post-surgical pain) |

The examples and embodiments described herein are for illustrative purposes only and in some embodiments, various modifications or changes are to be included within the purview of the disclosure and scope of the appended claims.

What is claimed is:

1. A method of treating or preventing pain in a subject in need thereof, comprising administering to the subject in need thereof an effective dose of (E)-2-methoxy-4-((8-methylnon-6-enamido)methyl)phenyl 2-((methylamino)methyl)piperidine-1-carboxylate hydrochloride (Compound 1), wherein the pain is: 1) post-surgical pain from a laparotomy, thoracotomy, thoraco-abdominal incision, flank incision, total hip replacement, total knee replacement, ACL reconstruction, rotator cuff repair, bunionectomy, laparoscopy, dental extraction, or open reduction internal fixation of fractures, 2) traumatic injury pain from a long bone, short bone, flat bone, or irregular bone fracture, or 3) chronic pain associated with osteoarthritis of the knee; and wherein the effective dose of Compound 1 is from about 0.01 mg to about 250 mg.

2. The method of claim 1, wherein the effective dose of Compound 1 is from about 0.01 mg to about 200 mg.

3. The method of claim 1, wherein the effective dose of Compound 1 is from about 0.01 mg to about 150 mg.

4. The method of claim 1, wherein the effective dose of Compound 1 is from about 0.01 mg to about 100 mg.

5. The method of claim 1, wherein the effective dose of Compound 1 is from about 1.0 mg to about 100 mg.

6. The method of claim 1, wherein the pain is post-surgical pain from a laparotomy, thoracotomy, thoraco-abdominal incision, flank incision, total hip replacement, total knee replacement, ACL reconstruction, rotator cuff repair, bunionectomy, laparoscopy, dental extraction, or open reduction internal fixation of fractures.

7. The method of claim 1, wherein the pain is traumatic injury pain from a long bone, short bone, flat bone, or irregular bone fracture.

8. The method of claim 1, wherein the pain is chronic pain associated with osteoarthritis of the knee.

* * * * *